(12) United States Patent
Gousse et al.

(10) Patent No.: US 10,806,821 B2
(45) Date of Patent: *Oct. 20, 2020

(54) HEAT STABLE HYALURONIC ACID COMPOSITIONS FOR DERMATOLOGICAL USE

(71) Applicant: Allergan Industrie, SAS, Pringy (FR)

(72) Inventors: Cecile Gousse, Dingy Saint Clair (FR); Pierre F. Lebreton, Annecy (FR); Nicholas Prost, Mornant (FR)

(73) Assignee: ALLERGAN INDUSTRIE, SAS, Pringy (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/290,274

(22) Filed: Mar. 1, 2019

(65) Prior Publication Data

US 2019/0192732 A1 Jun. 27, 2019

Related U.S. Application Data

(63) Continuation of application No. 15/825,465, filed on Nov. 29, 2017, now Pat. No. 10,220,113, which is a continuation of application No. 15/099,016, filed on Apr. 14, 2016, now Pat. No. 9,855,367, which is a continuation of application No. 13/675,993, filed on Nov. 13, 2012, now Pat. No. 9,333,160, which is a continuation of application No. 12/714,377, filed on Feb. 26, 2010, now abandoned, which is a continuation-in-part of application No. 12/687,048, filed on Jan. 13, 2010, now abandoned.

(51) Int. Cl.
*A61L 27/20* (2006.01)
*A61K 8/73* (2006.01)
*A61Q 19/00* (2006.01)
*A61Q 19/08* (2006.01)
*A61K 8/41* (2006.01)
*A61K 8/42* (2006.01)
*A61L 27/00* (2006.01)
*A61L 27/54* (2006.01)

(52) U.S. Cl.
CPC .............. *A61L 27/20* (2013.01); *A61K 8/415* (2013.01); *A61K 8/42* (2013.01); *A61K 8/73* (2013.01); *A61K 8/735* (2013.01); *A61L 27/00* (2013.01); *A61L 27/54* (2013.01); *A61Q 19/00* (2013.01); *A61Q 19/08* (2013.01); *A61L 2300/204* (2013.01); *A61L 2300/232* (2013.01); *A61L 2300/402* (2013.01)

(58) Field of Classification Search
CPC .............. A61K 2300/00; A61K 31/728; A61K 31/737; A61K 45/06
See application file for complete search history.

(56) References Cited

U.S. PATENT DOCUMENTS

| 2,128,827 A | 8/1938 | Killian |
| 3,548,056 A | 12/1970 | Eigen et al. |
| 3,763,009 A | 10/1973 | Suzuki et al. |
| 3,949,073 A | 4/1976 | Daniels et al. |
| 4,060,081 A | 11/1977 | Yannas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs et al. |
| 4,642,117 A | 2/1987 | Nguyen et al. |
| 4,657,553 A | 4/1987 | Taylor |
| 4,713,448 A | 12/1987 | Balazs et al. |
| 4,716,154 A | 12/1987 | Malson et al. |
| 4,772,419 A | 9/1988 | Malson et al. |
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,084,563 A | 1/1992 | Sakai et al. |
| 5,087,446 A | 2/1992 | Suzuki et al. |
| 5,091,171 A | 2/1992 | Yu et al. |
| 5,137,723 A | 8/1992 | Yamamoto et al. |

(Continued)

FOREIGN PATENT DOCUMENTS

| CA | 0949965 A1 | 6/1974 |
| CA | 2805008 | 1/2012 |

(Continued)

OTHER PUBLICATIONS

Adams, Mark, An Analysis of Clinical Studies of the Use of Crosslinked Hyaluronan, Hylan, in the Treatment of Osteoarthritis, The Journal of Rheumatology, 1993, 16-18, 20 (39).
Aesthetic Buyers Guide, Juvederm Raises Standards, 2007, 1, 4-7; www.miinews.com.
Albano, Emanuele et al., Hydroxyethyl Radicals in Ethanol Hepatotoxicity, Frontiers in Bioscience, 1999, 533-540, 4.
Allemann, Inja Bogdan, Hyaluronic Acid Gel (Juvederm) Preparations in the Treatment of Facial Wrinkles and Folds, Clinical Interventions in Aging, 2008, 629-634, 3 (4).
American Society for Aesthetic Plastic Surgery, http://www.surgery.org/media/news-release/115-million-cosmetic-procedures-in-2006; Mar. 9, 2007.

(Continued)

*Primary Examiner* — Michael B. Pallay
(74) *Attorney, Agent, or Firm* — Nathan S. Smith; Christopher J. Betti; Morgan, Lewis & Bockius LLP

(57) ABSTRACT

The disclosure provides hyaluronic acid (HA) gel formulations and methods for treating the appearance of the skin. The formulations contain hyaluronic acid and at least one additional ingredient. Methods for treating lines, wrinkles, fibroblast depletions, and scars with the disclosed composition are provided as well.

19 Claims, 7 Drawing Sheets

(56) References Cited

U.S. PATENT DOCUMENTS

| | | |
|---|---|---|
| 5,143,724 A | 9/1992 | Leshchiner et al. |
| 5,246,698 A | 9/1993 | Leshchiner et al. |
| 5,252,722 A | 10/1993 | Mandai et al. |
| 5,272,136 A | 12/1993 | Mandai et al. |
| 5,278,059 A | 1/1994 | Sugimoto et al. |
| 5,314,874 A | 5/1994 | Miyata et al. |
| 5,328,955 A | 7/1994 | Rhee et al. |
| 5,338,420 A | 8/1994 | Aga et al. |
| 5,356,883 A | 10/1994 | Kuo et al. |
| 5,399,351 A | 3/1995 | Leshchiner et al. |
| 5,407,812 A | 4/1995 | Sakai et al. |
| 5,428,024 A | 6/1995 | Chu et al. |
| 5,432,161 A | 7/1995 | Sakai et al. |
| 5,468,850 A | 11/1995 | Mandai et al. |
| 5,508,391 A | 4/1996 | Sakai et al. |
| 5,531,716 A | 7/1996 | Luzio et al. |
| 5,545,587 A | 8/1996 | Sugimoto et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamato et al. |
| 5,616,689 A | 4/1997 | Shenoy et al. |
| 5,630,923 A | 5/1997 | Aga et al. |
| 5,633,001 A | 5/1997 | Agerup |
| 5,643,464 A | 7/1997 | Rhee et al. |
| 5,676,964 A | 10/1997 | Della Valle et al. |
| 5,750,141 A | 5/1998 | Roberts |
| 5,759,532 A | 6/1998 | Galin et al. |
| 5,767,149 A | 6/1998 | Yamamoto et al. |
| 5,823,671 A | 10/1998 | Mitchell et al. |
| 5,824,333 A | 10/1998 | Scopelianos et al. |
| 5,827,529 A | 10/1998 | Ono et al. |
| 5,843,907 A | 12/1998 | Sakai et al. |
| 5,880,107 A | 3/1999 | Buenter |
| 5,886,042 A | 3/1999 | Yu et al. |
| 5,935,164 A | 8/1999 | Iverson |
| 5,972,326 A | 10/1999 | Galin et al. |
| 5,972,385 A | 10/1999 | Liu et al. |
| 5,980,930 A | 11/1999 | Fenton et al. |
| 6,013,679 A | 1/2000 | Kuo et al. |
| 6,066,325 A | 5/2000 | Wallace et al. |
| 6,129,761 A | 10/2000 | Hubbell |
| 6,224,857 B1 | 5/2001 | Romeo et al. |
| 6,248,905 B1 | 6/2001 | Fujinami et al. |
| 6,319,260 B1 | 11/2001 | Yamamoto |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,444,647 B1 | 9/2002 | Robinson et al. |
| 6,495,148 B1 | 12/2002 | Abbiati |
| 6,521,223 B1 | 2/2003 | Calias et al. |
| 6,544,503 B1 | 4/2003 | Vanderhoff et al. |
| 6,576,446 B2 | 6/2003 | Yamasaki et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci et al. |
| 6,767,924 B2 | 7/2004 | Yu et al. |
| 6,767,928 B1 | 7/2004 | Murphy et al. |
| 6,852,255 B2 | 2/2005 | Yang et al. |
| 6,893,466 B2 | 5/2005 | Trieu |
| 6,903,199 B2 | 6/2005 | Moon et al. |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 6,991,652 B2 | 1/2006 | Burg |
| 7,015,198 B1 | 3/2006 | Orentreich |
| 7,119,062 B1 | 10/2006 | Alvis et al. |
| 7,129,209 B2 | 10/2006 | Rhee |
| 7,166,570 B2 | 1/2007 | Hunter et al. |
| 7,192,984 B2 | 3/2007 | Berg et al. |
| 7,196,180 B2 | 3/2007 | Aeschlimann et al. |
| 7,314,636 B2 | 1/2008 | Caseres et al. |
| 7,316,822 B2 | 1/2008 | Binette |
| 7,491,709 B2 | 2/2009 | Carey |
| 7,741,476 B2 | 6/2010 | Lebreton |
| 7,767,452 B2 | 8/2010 | Kleinsek |
| 7,799,767 B2 | 9/2010 | Lamberti et al. |
| 7,812,049 B2 | 10/2010 | Shanler et al. |
| 7,875,296 B2 | 1/2011 | Binette |
| 7,902,171 B2 | 3/2011 | Reinmueller et al. |
| 8,052,990 B2 | 11/2011 | Hermitte et al. |
| 8,053,423 B2 | 11/2011 | Lamberti et al. |
| 8,114,898 B2 | 2/2012 | Shanler et al. |
| 8,124,120 B2 | 2/2012 | Sadozai et al. |
| 8,137,702 B2 | 3/2012 | Binette et al. |
| 8,153,591 B2 | 4/2012 | Masters et al. |
| 8,288,347 B2 | 10/2012 | Collette et al. |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 8,394,782 B2 | 3/2013 | Strompoulis |
| 8,394,783 B2 | 3/2013 | Strompoulis |
| 8,394,784 B2 | 3/2013 | Stroumpoulis et al. |
| 8,455,465 B2 | 6/2013 | Molliard |
| 8,512,752 B2 | 8/2013 | Crescenzi et al. |
| 8,513,216 B2 | 8/2013 | Strompoulis |
| 8,524,213 B2 | 9/2013 | Leshchiner et al. |
| 8,563,532 B2 | 10/2013 | Lebreton |
| 8,575,129 B2 | 11/2013 | Bellini |
| 8,586,562 B2 | 11/2013 | Lebreton |
| 8,853,184 B2 | 10/2014 | Strompoulis |
| 8,946,192 B2 | 2/2015 | Gousse et al. |
| 9,333,160 B2* | 5/2016 | Gousse .................. A61K 8/735 |
| 9,655,991 B2* | 5/2017 | Gousse .................. A61L 27/20 |
| 9,662,422 B2 | 5/2017 | Pollock et al. |
| 9,855,367 B2* | 1/2018 | Gousse .................. A61K 8/735 |
| 10,220,113 B2* | 3/2019 | Gousse .................. A61K 8/735 |
| 10,449,268 B2* | 10/2019 | Gousse .................. A61L 27/54 |
| 2001/0039336 A1 | 11/2001 | Miller et al. |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0013729 A1 | 1/2005 | Brown-Skrobot |
| 2005/0025755 A1 | 2/2005 | Hedrick et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0165079 A1 | 7/2005 | Shanler |
| 2005/0181007 A1 | 8/2005 | Hunter et al. |
| 2005/0186261 A1 | 8/2005 | Avelar et al. |
| 2005/0186673 A1 | 8/2005 | Geistlich et al. |
| 2005/0226936 A1 | 10/2005 | Agerup |
| 2005/0227936 A1 | 10/2005 | McSwiggen et al. |
| 2005/0240147 A1 | 10/2005 | Makower |
| 2005/0271729 A1 | 12/2005 | Wang |
| 2005/0276830 A1 | 12/2005 | DeJovin et al. |
| 2005/0281880 A1 | 12/2005 | Wang |
| 2005/0287180 A1 | 12/2005 | Chen |
| 2006/0029578 A1 | 2/2006 | Hoemann et al. |
| 2006/0040894 A1* | 2/2006 | Hunter .................. A61K 31/19 514/54 |
| 2006/0095137 A1 | 5/2006 | Chung et al. |
| 2006/0105022 A1 | 5/2006 | Yokokawa et al. |
| 2006/0122147 A1 | 6/2006 | Wohlrab |
| 2006/0141049 A1 | 6/2006 | Lyons |
| 2006/0147483 A1 | 7/2006 | Chaouk et al. |
| 2006/0189516 A1 | 8/2006 | Yang et al. |
| 2006/0194758 A1 | 8/2006 | Lebreton |

(56) References Cited

U.S. PATENT DOCUMENTS

| | | |
|---|---|---|
| 2006/0246137 A1 | 11/2006 | Hermitte et al. |
| 2006/0247722 A1 | 11/2006 | Maschino |
| 2006/0257488 A1 | 11/2006 | Hubbard |
| 2006/0264515 A1 | 11/2006 | Dejovin et al. |
| 2006/0286769 A1 | 12/2006 | Tsuchiya et al. |
| 2007/0026070 A1 | 2/2007 | Vonwiller et al. |
| 2007/0036745 A1 | 2/2007 | Leshchiner et al. |
| 2007/0066816 A1 | 3/2007 | Tsai et al. |
| 2007/0077292 A1 | 4/2007 | Pinsky |
| 2007/0082070 A1 | 4/2007 | Stookey |
| 2007/0104692 A1 | 5/2007 | Quijano et al. |
| 2007/0104693 A1 | 5/2007 | Quijano et al. |
| 2007/0203095 A1 | 8/2007 | Sadozai et al. |
| 2007/0212385 A1 | 9/2007 | David |
| 2007/0224247 A1 | 9/2007 | Chudzik et al. |
| 2007/0224278 A1 | 9/2007 | Lyons et al. |
| 2007/0298005 A1 | 12/2007 | Marie-Josee |
| 2008/0044476 A1 | 2/2008 | Lyons et al. |
| 2008/0050335 A1 | 2/2008 | Faour et al. |
| 2008/0057091 A1 | 3/2008 | Abdellaoui et al. |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0241252 A1 | 10/2008 | Lyons et al. |
| 2008/0268051 A1 | 10/2008 | Hughes et al. |
| 2008/0268547 A1 | 10/2008 | Avent |
| 2008/0274946 A1 | 11/2008 | Giampapa |
| 2008/0279806 A1 | 11/2008 | Cho |
| 2008/0293637 A1 | 11/2008 | Schroeder et al. |
| 2008/0300681 A1 | 12/2008 | Rigotti et al. |
| 2009/0017091 A1 | 1/2009 | Daniloff et al. |
| 2009/0018102 A1 | 1/2009 | Moutet et al. |
| 2009/0022808 A1 | 1/2009 | Champion et al. |
| 2009/0028817 A1 | 1/2009 | Niklason et al. |
| 2009/0036403 A1 | 2/2009 | Stroumpoulis et al. |
| 2009/0042834 A1 | 2/2009 | Karageozian |
| 2009/0054638 A1 | 2/2009 | Shelby |
| 2009/0060852 A1 | 3/2009 | DeJovin et al. |
| 2009/0093755 A1 | 4/2009 | Schroeder et al. |
| 2009/0098177 A1 | 4/2009 | Werkmeister et al. |
| 2009/0110671 A1 | 4/2009 | Miyata et al. |
| 2009/0110736 A1 | 4/2009 | Boutros |
| 2009/0123547 A1 | 5/2009 | Hill et al. |
| 2009/0124552 A1 | 5/2009 | Hill et al. |
| 2009/0130027 A1 | 5/2009 | Shanler et al. |
| 2009/0143331 A1 | 6/2009 | Stroumpoulis et al. |
| 2009/0143348 A1 | 6/2009 | Tezel et al. |
| 2009/0148527 A1 | 6/2009 | Robinson et al. |
| 2009/0155314 A1 | 6/2009 | Tezel et al. |
| 2009/0155362 A1 | 6/2009 | Longin et al. |
| 2009/0162415 A1 | 6/2009 | Huang et al. |
| 2009/0169615 A1 | 7/2009 | Pinsky |
| 2009/0181104 A1 | 7/2009 | Rigotti et al. |
| 2009/0192533 A1 | 7/2009 | Dlugos |
| 2009/0192541 A1 | 7/2009 | Ortiz |
| 2009/0222065 A1 | 9/2009 | Dlugos |
| 2009/0263447 A1 | 10/2009 | Asius et al. |
| 2009/0291986 A1 | 11/2009 | Puppas et al. |
| 2009/0297632 A1 | 12/2009 | Waugh |
| 2009/0317376 A1 | 12/2009 | Zukowska et al. |
| 2010/0004198 A1 | 1/2010 | Stroumpoulis et al. |
| 2010/0028437 A1 | 2/2010 | Lebreton |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0130502 A1 | 5/2010 | DeJovin et al. |
| 2010/0136070 A1 | 6/2010 | Dobak et al. |
| 2010/0160948 A1 | 6/2010 | Rigotti et al. |
| 2010/0161052 A1 | 6/2010 | Rigotti et al. |
| 2010/0168780 A1 | 7/2010 | Rigotti et al. |
| 2010/0226982 A1 | 9/2010 | Malessa |
| 2010/0226988 A1 | 9/2010 | Lebreton |
| 2010/0227867 A1 | 9/2010 | DeJovin |
| 2010/0247651 A1 | 9/2010 | Kestler |
| 2010/0249924 A1 | 9/2010 | Powell et al. |
| 2010/0255068 A1 | 10/2010 | Stroumpoulis et al. |
| 2010/0291171 A1 | 11/2010 | Crescenzi et al. |
| 2010/0316683 A1 | 12/2010 | Piron et al. |
| 2011/0008406 A1 | 1/2011 | Altman et al. |
| 2011/0008436 A1 | 1/2011 | Altman et al. |
| 2011/0008437 A1 | 1/2011 | Altman et al. |
| 2011/0014263 A1 | 1/2011 | Altman et al. |
| 2011/0014287 A1 | 1/2011 | Altman et al. |
| 2011/0020409 A1 | 1/2011 | Altman et al. |
| 2011/0034684 A1 | 2/2011 | Yokokawa et al. |
| 2011/0052695 A1 | 3/2011 | Jiang et al. |
| 2011/0070281 A1 | 3/2011 | Altman |
| 2011/0077737 A1 | 3/2011 | Stroumpoulis et al. |
| 2011/0091726 A1 | 4/2011 | Shibuya et al. |
| 2011/0097381 A1 | 4/2011 | Altman |
| 2011/0104800 A1 | 5/2011 | Kensy et al. |
| 2011/0111031 A1 | 5/2011 | Jiang et al. |
| 2011/0118206 A1 | 5/2011 | Lebreton |
| 2011/0150823 A1 | 6/2011 | Huang |
| 2011/0150846 A1 | 6/2011 | Van Epps |
| 2011/0171286 A1 | 7/2011 | Cecile et al. |
| 2011/0171310 A1 | 7/2011 | Gousse |
| 2011/0171311 A1 | 7/2011 | Gousse et al. |
| 2011/0172180 A1 | 7/2011 | Gousse et al. |
| 2011/0183001 A1 | 7/2011 | Rosson |
| 2011/0183406 A1 | 7/2011 | Kensy |
| 2011/0189292 A1 | 8/2011 | Lebreton |
| 2011/0194945 A1 | 8/2011 | Kensy et al. |
| 2011/0201571 A1 | 8/2011 | Gavard |
| 2011/0224164 A1 | 9/2011 | Lebreton |
| 2011/0224216 A1 | 9/2011 | Andres |
| 2011/0229574 A1 | 9/2011 | Guillen et al. |
| 2011/0286945 A1 | 11/2011 | DeJovin et al. |
| 2011/0288096 A1 | 11/2011 | Graeber et al. |
| 2011/0295238 A1 | 12/2011 | Kensy et al. |
| 2012/0010146 A1 | 1/2012 | Han et al. |
| 2012/0034462 A1 | 2/2012 | Stroumpoulis et al. |
| 2012/0045420 A1 | 2/2012 | Van Epps et al. |
| 2012/0071437 A1 | 3/2012 | Stroumpoulis et al. |
| 2012/0076868 A1 | 3/2012 | Lamberti et al. |
| 2012/0095206 A1 | 4/2012 | Chen |
| 2012/0100217 A1 | 4/2012 | Green |
| 2012/0100611 A1 | 4/2012 | Kensy et al. |
| 2012/0135937 A1 | 5/2012 | Bertholon et al. |
| 2012/0156265 A1 | 6/2012 | Binette et al. |
| 2012/0164098 A1 | 6/2012 | Schroeder et al. |
| 2012/0164116 A1 | 6/2012 | Van Epps |
| 2012/0165935 A1 | 6/2012 | Van Epps |
| 2012/0171265 A1 | 7/2012 | Altman et al. |
| 2012/0172317 A1 | 7/2012 | Altman et al. |
| 2012/0172328 A1 | 7/2012 | Lebreton |
| 2012/0172985 A1 | 7/2012 | Altman et al. |
| 2012/0189589 A1 | 7/2012 | Van Epps et al. |
| 2012/0189590 A1 | 7/2012 | Van Epps et al. |
| 2012/0189591 A1 | 7/2012 | Van Epps et al. |
| 2012/0189699 A1 | 7/2012 | Stroumpoulis et al. |
| 2012/0189708 A1 | 7/2012 | Van Epps et al. |
| 2012/0190644 A1 | 7/2012 | D'este |
| 2012/0207837 A1 | 8/2012 | Powell et al. |
| 2012/0208890 A1 | 8/2012 | Gousse et al. |
| 2012/0209381 A1 | 8/2012 | Powell et al. |
| 2012/0213852 A1 | 8/2012 | Van Epps et al. |
| 2012/0213853 A1 | 8/2012 | Van Epps et al. |
| 2012/0219627 A1 | 8/2012 | Van Epps et al. |
| 2012/0225842 A1 | 9/2012 | Gousse et al. |
| 2012/0232030 A1 | 9/2012 | Gousse et al. |
| 2012/0263686 A1 | 10/2012 | Van Epps et al. |
| 2012/0265297 A1 | 10/2012 | Altman et al. |
| 2012/0269777 A1 | 10/2012 | Van Epps et al. |
| 2012/0283428 A1 | 11/2012 | Lee et al. |
| 2012/0295870 A1 | 11/2012 | Lebreton |
| 2013/0023658 A1 | 1/2013 | Stroumpoulis et al. |
| 2013/0041038 A1 | 2/2013 | Lebreton |
| 2013/0041039 A1 | 2/2013 | Lebreton |

(56) References Cited

U.S. PATENT DOCUMENTS

| | | |
|---|---|---|
| 2013/0072453 A1 | 3/2013 | Gousse et al. |
| 2013/0096081 A1 | 4/2013 | Njikang |
| 2013/0116188 A1 | 5/2013 | Pollock et al. |
| 2013/0116190 A1 | 5/2013 | Pollock et al. |
| 2013/0116411 A1 | 5/2013 | Pollock et al. |
| 2013/0123210 A1 | 5/2013 | Liu |
| 2013/0129835 A1 | 5/2013 | Pollock et al. |
| 2013/0131011 A1 | 5/2013 | Lebreton |
| 2013/0131655 A1 | 5/2013 | Rigotti et al. |
| 2013/0136780 A1 | 5/2013 | Tezel et al. |
| 2013/0203696 A1 | 8/2013 | Liu |
| 2013/0203856 A1 | 8/2013 | Cho, II |
| 2013/0209532 A1 | 8/2013 | Stroumpoulis et al. |
| 2013/0210760 A1 | 8/2013 | Liu |
| 2013/0237615 A1 | 9/2013 | Meunier |
| 2013/0244943 A1 | 9/2013 | Yu et al. |
| 2013/0244970 A1 | 9/2013 | Lebreton |
| 2013/0274222 A1 | 10/2013 | Horne |
| 2013/0287758 A1 | 10/2013 | Tozzi |
| 2014/0011990 A1 | 1/2014 | Lebreton |
| 2014/0227235 A1 | 8/2014 | Kim et al. |
| 2016/0113855 A1 | 4/2016 | Njikang |
| 2017/0273886 A1 | 9/2017 | Gousse |

FOREIGN PATENT DOCUMENTS

| | | |
|---|---|---|
| CA | 2786968 A1 | 2/2018 |
| CN | 102548590 | 7/2012 |
| EP | 0273823 A1 | 7/1988 |
| EP | 0416250 A2 | 3/1991 |
| EP | 0416846 A2 | 3/1991 |
| EP | 0555898 | 10/1993 |
| EP | 0648229 A1 | 4/1995 |
| EP | 1247522 A1 | 10/2002 |
| EP | 1398131 A1 | 3/2004 |
| EP | 1419792 A1 | 5/2004 |
| EP | 1115433 | 12/2004 |
| EP | 1532991 A1 | 5/2005 |
| EP | 1726299 A2 | 11/2006 |
| EP | 1932530 | 6/2008 |
| EP | 2236523 A1 | 6/2010 |
| EP | 2435045 | 4/2012 |
| EP | 2435083 A2 | 4/2012 |
| EP | 2484387 | 8/2012 |
| EP | 2207424 | 6/2014 |
| EP | 2523701 B1 | 9/2016 |
| FR | 2733427 B1 | 10/1996 |
| FR | 2752843 | 3/1998 |
| FR | 2920000 B1 | 2/2009 |
| FR | 2924615 B1 | 6/2009 |
| JP | 650153711 A | 11/1980 |
| JP | 2001192336 | 7/2001 |
| JP | 2002-080501 | 3/2002 |
| JP | 2006523731 | 10/2006 |
| JP | 2007502645 | 2/2007 |
| JP | 2007063177 A | 3/2007 |
| JP | 2007525541 | 9/2007 |
| JP | 2010511454 | 4/2010 |
| JP | 2010202522 | 9/2010 |
| JP | 2012508217 | 4/2012 |
| KR | 20110138765 | 12/2011 |
| KR | 20130018518 | 2/2013 |
| WO | 1986000079 A1 | 1/1986 |
| WO | 1986000912 A1 | 2/1986 |
| WO | 1992000105 A1 | 1/1992 |
| WO | 1992020349 A1 | 11/1992 |
| WO | 1996033751 A1 | 10/1993 |
| WO | 1994001468 A1 | 1/1994 |
| WO | 1994002517 A1 | 3/1994 |
| WO | 1996033709 A1 | 10/1996 |
| WO | 1997004012 A1 | 6/1997 |
| WO | 1998035639 A1 | 8/1998 |
| WO | 1998035640 A1 | 8/1998 |
| WO | 1999-049878 | 10/1999 |
| WO | 2000001428 A1 | 1/2000 |
| WO | WO 00/08061 | 2/2000 |
| WO | WO 00/46252 | 8/2000 |
| WO | 2001079342 A2 | 10/2001 |
| WO | 2002005753 A1 | 1/2002 |
| WO | 2002006350 A1 | 1/2002 |
| WO | 2002009792 A1 | 2/2002 |
| WO | 2003007782 A2 | 1/2003 |
| WO | 2002017713 A1 | 3/2003 |
| WO | 2004020473 A1 | 3/2004 |
| WO | 2004022603 A1 | 3/2004 |
| WO | WO 2004/067575 | 8/2004 |
| WO | 2004073759 A1 | 9/2004 |
| WO | 2004092223 A1 | 10/2004 |
| WO | 2005040224 A1 | 6/2005 |
| WO | WO 2005/052035 | 6/2005 |
| WO | 2005067994 A1 | 7/2005 |
| WO | 2005074913 A2 | 8/2005 |
| WO | 2005112888 A2 | 12/2005 |
| WO | WO 2006/015490 | 2/2006 |
| WO | 2006-031555 A2 | 3/2006 |
| WO | 2006023645 A2 | 3/2006 |
| WO | WO 2006/021644 | 3/2006 |
| WO | WO 2006/048671 | 5/2006 |
| WO | 2006067608 A1 | 6/2006 |
| WO | WO 2006/056204 | 6/2006 |
| WO | 2006-102626 A2 | 9/2006 |
| WO | 2007018124 A1 | 2/2007 |
| WO | 2007070617 A1 | 6/2007 |
| WO | 2007077399 A3 | 7/2007 |
| WO | 2007128923 A3 | 11/2007 |
| WO | 2007136738 A2 | 11/2007 |
| WO | 2008-015249 | 2/2008 |
| WO | 2008034176 A1 | 3/2008 |
| WO | WO2008031525 A1 | 3/2008 |
| WO | WO 2008/063569 | 5/2008 |
| WO | 2008068297 A1 | 6/2008 |
| WO | 2008072230 A1 | 6/2008 |
| WO | 2008077172 A2 | 7/2008 |
| WO | 2008-098019 | 8/2008 |
| WO | 2008098019 A2 | 8/2008 |
| WO | 2008139122 A2 | 11/2008 |
| WO | 2008148967 A3 | 12/2008 |
| WO | 2008157608 A1 | 12/2008 |
| WO | WO 2008/148071 | 12/2008 |
| WO | WO 2009/003135 | 12/2008 |
| WO | 2009-005790 A2 | 1/2009 |
| WO | 2009024719 A1 | 2/2009 |
| WO | 2009026158 A3 | 2/2009 |
| WO | WO 2009/024350 | 2/2009 |
| WO | 2009028764 A1 | 3/2009 |
| WO | 2009034559 A2 | 3/2009 |
| WO | 2009073437 A1 | 6/2009 |
| WO | 2009082354 A1 | 7/2009 |
| WO | 2010003797 A1 | 1/2010 |
| WO | WO 2010/003104 | 1/2010 |
| WO | 2010-015901 A1 | 2/2010 |
| WO | 2010015900 A1 | 2/2010 |
| WO | 2010027471 A2 | 3/2010 |
| WO | 2010028025 A1 | 3/2010 |
| WO | 2010029344 A3 | 3/2010 |
| WO | WO 2010/026299 | 3/2010 |
| WO | 2010038771 A1 | 4/2010 |
| WO | 2010051641 A1 | 5/2010 |
| WO | 2010052430 A1 | 5/2010 |
| WO | 2010053918 A1 | 5/2010 |
| WO | 2010061005 A1 | 6/2010 |
| WO | 2010-136585 | 12/2010 |
| WO | 2010-136594 | 12/2010 |
| WO | WO 2011/023355 | 3/2011 |
| WO | WO 2011/072399 | 6/2011 |
| WO | 2011-086458 | 7/2011 |
| WO | WO 2011/135150 | 11/2011 |
| WO | WO 2012/008722 | 1/2012 |
| WO | WO 2012/077055 | 6/2012 |
| WO | 2012-104419 | 8/2012 |
| WO | 2012-113529 A1 | 8/2012 |
| WO | WO 2013/015579 | 1/2013 |

(56) References Cited

FOREIGN PATENT DOCUMENTS

| WO | WO 2013/036568 | 3/2013 |
|---|---|---|
| WO | WO 2013/067293 | 5/2013 |
| WO | WO 2013/086024 | 6/2013 |

OTHER PUBLICATIONS

Anatelli, Florencia et al, Amorphous Basophilic Deposit in the Superficial Dermis of the Lip in an 80 Year Old, Am J Dermatophathol, 2010, 306-309, 32(3).
Antunes, et al., Efficacy of Intrarectal Lidocaine Hydrochloride Gel for Pain Control in Patients Undergoing Transrectal Prostate Biopsy, International Brazilian Journal of Urology, Sep./Oct. 2004, 380-383, vol. 30, Issue 5, Brazilian Society of Urology.
Atanassoff, et al., The Effect of Intradermal Administration of Lidocaine and Morphine on the Response to Thermal Stimulation, Anesthesia and Analgesia, 1997, 1340-1343, vol. 84, Issue 6.
Basran, G.S. et al, Adrenoceptor-Agonist Inhibition of the Histamine-Induced Cutaneuos Response in Man, British Journal of Dermatology, 1982, 140-142, 107.
Baumann, et al., Comparison of Smooth-Gel Hyaluronic Acid Dermal Fillers with Cross-linked Bovine Collagen: A Multicenter, Double-Masked, Randomized, Within-Subject Study, Dermatologic Surgery, Dec. 2007, S128-S135, vol. 33, Suppl. 2, American Society of Dermatologic Surgery, Inc.
Beasley, Karen et al., Hyaluronic Acid Fillers: A Comprehensive Review, Facial Plastic Surgery, 2009, 86-94, 25 (2), Thieme Medical Publishers, Inc.
Beasley, Karen et al., Soft Tissue Augmentation Using a Two-Way Connector to Supplement Hyaluronic Acid Filler with 1% Lidocaine Hydrochloric Acid With Epinephrine 1:100000: Our Experience and Observations, Dermatol Surg, 2008, 524-526, 35.
Beer, Dermal Fillers and Combinations of Fillers for Facial Rejuvenation, Dermatologic Clinics, 2009, 427-432, 27 (4).
Belda, Jose et al., Hyaluronic Acid Combined With Mannitol to Improve Protection Against Free-Radical Endothelial Damage: Experimental Model, Journal of Cataract Refract Surg, 2005, 1213-1218, 31, Elsevier Inc.
Bircher, Andres et al., Delayed-type Hypersensitivity to Subcutaneous Lidocaine With Tolerance to Articaine: Confirmation by In Vivo and In Vitro Tests, Contact Dermatitis, 1996, 387-389, 34, Blackwell Publishing Ltd., Denmark.
Bluel, K. et al., Evaluation of Reconstituted Collagen Tape as a Model for Chemically Modified Soft Tissues, Biomat. Med. Dev. Art. Org., 1981, 37-46, 9 (1), Marcel Dekker, Inc.
Buck, Donald, Injectable Fillers For Facial Rejuvenation: A Review, Journal of Plastic, Reconstructive & Aesthetic Surgery, 2009, 11-18, 62, Elsevier.
Busso, Mariano et al, An Investigation of Changes in Physical Properties of Injectable Calcium Hydroxylapatite in a Carrier Gel When Mixed with Lidocaine and with Lidocaine/Epinephrine, Dermatol Surg, 2008, S16-S24, 34.
Capozzi, Angelo et al., Distant Migration of Silicone Gel From a Ruptured Breast Implant, Silicone Gel Migration, 1978, 302-3, 62 (2).
Carlin, G. et al., Effect of Anti-Inflammatory Drugs on Xanthine Oxidase and Xanthine Oxidase Induced Depolymerization of Hyaluronic Acid, Agents and Actions, 1985, 377-384, 16 (5), Birkhauser Verlag, Basel.
Carruthers, Alastair et al, Botulinum Toxin Type A: History and Current Cosmetic Use in the Upper Face, Semin Cutan Med Surg, 2001, 71-84, 20(2).
Carruthers, et al., The Science and Art of Dermal Fillers for Soft-Tissue Augmentation, Journal of Drugs in Dermatology, Apr. 2009, 335-350, vol. 8, Issue 4.
Carruthers, Jean et al, Volumizing the Glabella and Forehead, Dermatol Surg, 2010, 1905-1909, 36.
Cassidy, James et al, Epinephrine: Systemic Effects and Varying Concentrations in Local Anesthesia, Anesth Prog, 1986, 289-297, 33(6).
Champion, et al., Role of Target Geometry in Phagocytosis, Proc. National Academy of Sciences, 2006, 4930-4934, 103 (13), The National Academy of Sciences of the USA.
Chemical Abstract Registry, RN 220644-17-7, RN 39479-63-5, 1 Page, 2016.
Chin, et al., Allergic Hypersensitivity to Lidocaine Hydrochloride, International Journal of Dermatology, 1980, 147-148, vol. 19, International Society of Topical Dermatology, Inc.
Chvapil, Milos, Collagen Sponge: Theory and Practice of Medical Applications, J. Biomed. Mater. Res., 1977, 721-741, 11, John Wiley & Sons, Inc.
Clark, et al., The Influence of Triamcinolone Acetonide on Joint Stiffness in the Rat, The Journal of Bone and Joint Surgery, Oct. 1971, 1409-1414, 53A (7).
Cohen, Miriam et al., Organization and Adhesive Properties of the Hyaluronan Pericellular Coat of Chondrocytes and Epithelial Cells, Biophysical Journal, Sep. 2003, 1996-2005, 85, Biophysical Society.
Cui, Yu et al., The Comparison of Physicochemical Properties of Four Cross-linked Sodium Hyaluronate Gels With Different Cross-linking Agents, Advanced Materials Research, 2012, 1506-1512, 396-398.
Deland, Frank, Intrathecal Toxicity Studies with Benzyl Alcohol, Toxicology and Applied Pharmacology, 1973, 153-6, 25, Academic Press, Inc.
Desai, et al., Molecular Weight of Heparin Using 13C Nuclear Magnetic Resonance Spectroscopy, Journal of Pharm Sci., Feb. 1995, 212-215, 84 (2).
Egbert, L.D. et al, Reduction of Bleeding by the Addition of Vasoconstrictor Drugs to Local Anesthetics, Annals of Surgery, 1962, 20-24, 155.
Eyre, et al., Collagen Cross-Links, Top Curr Chem, 2005, 207-229, 247, Springer-Verlag, Berlin Heidelberg.
Fagien, Steven, Variable Reconstitution of Injectable Hyaluronic Acid With Local Anesthetic for Expanded Applications in Facial Aesthetic Enhancement, Dermatol Surg, 2010, 815-821, 36.
Falcone, et al., Crosslinked Hyaluronic Acid Dermal Fillers: A Comparison of Rheological Properties, Journal of Biomedical Materials Research, 2008, 264-271, 87 (1), Wiley InterScience.
Falcone, Samuel et al., Temporary Polysaccharide Dermal Fillers: A Model for Persistence Based on Physical Properties, Dermatologic Surgery, 2009, 1238-1243, 35 (8).
Farley, et al., Diluting Lidocaine and Mepivacaine in Balanced Salt Solution Reduces the Pain of Intradermal Injection, Regional Anesthesia, 1994, 48-51, 19 (1).
Folwaczny, C. et al, Influence of Prophylactic Local Administration of Epinephrine on Bleeding Complications After Polypectomy, Endoscopy, 1996, 31-33, 28.
Frati, Elena et al., Degradation of Hyaluronic Acid by Photosensitized Riboflavin In Vitro. Modulation of the Effect by Transition Metals, Radical Quenchers, and Metal Chelators, Free Radical Biology Medicine, 1996, 1139-1144, 22 (7).
Fujinaga, Masahiko et al., Reproductive and Teratogenic Effects of Lidocaine in Sprague-Dawley Rats, Anesthesiology, 1986, 626-632, 65.
Fukuda, et al., English machine translation of JP 2007-063177 A, Mar. 15, 2007, translated Feb. 9, 2012 JST, pp. 1-10.
Funt, David, Avoiding Malar Edema During Midface/Check Augmentation with Dermal Fillers, J Clin Aesthet Dermatol, Dec. 2011, 32-36, 4(12).
Gammaitoni, et al., Pharmacokinetics and Safety of Continuously Applied Lidocaine Patches 5%, Am J Health Syst Pharm, 2002, 2215-2220, 59.
Gassner, Holger et al, Addition of an Anesthetic Agent to Enhance the Predictability of the Effects of Botulinum Toxin Type A Injections: A Randomized Controlled Study, Mayo Clin Proc, 2000, 701-704, 75(7).
Ginshicel MH, Hydroxy Propyl Methyl Cellulose, Retrieved on Nov. 12, 2008 http://www.ginshicel.cn/MHPC.html, 2007, p. 1-3, 2 (3).

(56) References Cited

OTHER PUBLICATIONS

Gold, Use of Hyaluronic Acid Fillers for the Treatment of the Aging Face, Clinical Interventions in Aging, 2007, 369-376, 2 (3), Dove Medical Press Limited.
Goldberg, David, Breakthroughs in US dermal fillers for facial soft-tissue augmentation, Journal of Cosmetic and Laser Therapy, 2009, 240-247, 11, Informa UK Ltd.
Graefe, et al., Sensitive and Specific Photometric Determination of Mannitol, Clinical Chemistry and Laboratory Medicine, 2003, 1049-1055, 41 (8), Walter de Gruyter.
Grecomoro, G. et al., Intra-articular treatment with sodium hyaluronate in gonarthrosis: a controlled clinical trial versus placebo, Pharmatherapeutica, 1987, 137-141, 5 (2).
Grillo, Hermes et al., Thermal Reconstitution of Collagen From Solution and the Response to Its Heterologous Implantation, JSR, 1962, 69-82, 2 (1).
Hantash, Basil et al, A Pilot Study on the Effect of Epinephrine on Botulinum Toxin Treatment for Periorbital Rhytides, Dermatologic Surgery, 2007, 461-468, 33.
Hassan, HG et al., Effects of Adjuvants to Local Anaesthetics on Their Duration. III. Experimental Studies of Hyaluronic Acid, Acta Anaesthesiol Scand., 1985, 1, 29 (4).
Hayashibara, AA2G, Sep. 23, 2007, Retrieved on Jan. 17, 2012, http://web.archive.org/web/20070923072010/http://www.hayashibara-intl.com/cosmetics/aa2g.html.
Helary, Christophe et al., Concentrated Collagen Hydrogels as Dermal Substitutes, Biomaterials, 2010, 481-490, 31.
Helliwell, Philip, Use of an objective measure of articular stiffness to record changes in finger joints after intra-articular injection of corticosteroid, Annals of Rheumatic Diseases, 1997, 71-73, 56.
Hertzberger-Ten, Cate et al., Intra-articular steroids in pauciarticular juvenile chronic arthritis, type 1, European Journal of Pediatrics, 1991, 170-172, 150.
Hetherington, NJ et al., Potential for Patient Harm from Intrathecal Administration of Preserved Solutions, Med J Aust., 2000, 1, 173(3).
Hong, Samin et al, Effect of Prophylactic Brimonidine Instillation on Bleeding During Strabismus Surgery in Adults, Am J Ophthalmol, 2007, 469-470, 144.
Hurst, E., Adhesive Arachnoiditis and Vascular Blockage Caused by Detergents and Other Chemical Irritants: An Experimental Study, J Path. Bact., 1955, 167, 70.
Intramed (Pty) Ltd, Intramed Mannitol 20% m/v Infusion, Package Insert, Jan. 1979, 4 pages, 12-214/8-94, ZA.
Jones, Adrian et al, Intra-articular Hyaluronic Acid Compared to Intra-articular Triamcinolone Hexacetonide in Inflammatory Knee Osteoarthritis, Osteoarthritis and Cartilage, 1995, 269-273, 3.
Jones, Derek, Semipermanent and Permanent Injectable Fillers, Dermatol Clin, 2009, 433-444, 27.
Kablik, et al., Comparative Physical Properties of Hyaluronic Acid Dermal Fillers, Dermatology Surgery, 2009, 302-312, 35, Wiley Periodicals, Inc.
Klein, A., Skin Filling Collagen and Other Injectables of the Skin, Fundamentals of Cosmetic Surgery, 2001, 491-508, 3 (19).
Kopp, et al., The Short-term Effect of Intra-articular Injections of Sodium Hyaluronate and Corticosteroid on Temporomandibular Joint Pain and Dysfunction, Journal of Oral and Maxillofacial Surgery, 1985, 429-435, 43.
Kulicke, Werner-Michael et al., Visco-Elastic Properties of Sodium Hyaluronate Solutions, Institute for Technical and Macromolecular Chemistry, 2008, 585-587, DE.
Laeschke, Klaus, Biocompatibility of Microparticles Into Soft Tissue Fillers, Semin Cutan Med Surg, 2004, 214-217, 23.
Lamar, PD et al., Antifibrosis Effect of Novel Gels in Anterior Ciliary Sclerotomy (ACS), 2002, 1 Page, The Association for Research in Vision and Ophthalmology, Inc.
Levy, Jaime et al., Lidocaine Hypersensitivity After Subconjunctival Injection, Can J Ophthalmol, 2006, 204-206, 41.
Lindgren, Bjorn et al, Inhibitory Effects of Clonidine on Allergic Reactions in Guinea-Pig Skin, European Journal of Pharmacology, 1987, 339-343, 134.
Lindvall, Sven et al., Influence of Various Compounds on the Degradation of Hyaluronic Acid by a Myeloperoxidase System, Chemico-Biological Interactions, 1994, 1-12, 90.
Lundeberg, T. et al, Epinephrine Reduces the Severity of Catheter-Induced Urethral Inflammation By Action at the α2-Adrenoceptors, British Journal of Urology, 1993, 349-352, 72.
Lupo, Mary, Hyaluronic Acid Fillers in Facial Rejuvenation, Seminars in Cutaneous Medicine and Surgery, 2006, 122-126, 25.
Mackley, Christine et al., Delayed-Type Hypersensitivity to Lidocaine, Arch Dermatol, 2003, 343-346, 139.
Mancinelli, Laviero et al., Intramuscular High-dose Triamcinolone Acetonide in the Treatment of Severe Chronic Asthma, West J Med, 1997, 322-329, 167 (5).
Maniglia-Ferreira, Claudio et al, Clinical Evaluation of the Use of Three Anesthetics in Endodontics, Acta Odontol Latinoam, 2009, 21-26, 22(1).
Martin, Donna et al, Fine Rhytides Treated with Porcine Collagen-Derived Filler Mixed with Anesthetic, Dermatol Surg, 2010, 270-272, 36(2).
Matsumoto, Alan et al., Reducing the Discomfort of Lidocaine Administration Through pH Buffering, Journal of Vascular and Interventional Radiology, 1994, 171-175, 5 (1).
McCarty, Daniel et al., Inflammatory Reaction after Intrasynovial Injection of Microcrystalline Adrenocorticosteroid Esters, Arthritis and Rheumatism, 1964, 359-367, 7 (4).
McCleland, Marcee et al., Evaluation of Artecoll Polymethylmethacrylate Implant for Soft-Tissue Augmentation: Biocompatibility and Chemical Characterization, Plastic & Reconstructive Surgery, 1997, 1466-1474, 100 (6).
McCracken, Hyaluronic Acid Gel (Restylane) Filler for Facial Rhytids: Lessons Learned From American Society of Ophthalmic Plastic and Reconstructive Surgery Member Treatment of 286 Patients, Ophthalmic Plastic and Reconstructive Surgery, 2006, 188-191, 22 (3).
McPherson, John et al., Development and Biochemical Characterization of Injectable Collagen, Journal of Dermatol Surg Oncol, 1988, 13-20, 14 (Suppl 1) 7.
Menon, Harikumar et al, Low Dose of Hyaluronidase to Treat Over Correction by HA Filler—A Case Report, Journal of Plastic, Reconstructive & Aesthetic Surgery, 2010, e416-e417, 63.
Millay, Donna et al., Vasoconstrictors in Facial Plastic Surgery, Arch Otolaryngol Head Neck Surg., 1991, 160-163, 117.
Naoum, Christos et al, Dermal Filler Materials and Botulin Toxin, International Journal of Dermatology, 2001, 609-621, 40.
Orvisky, E. et al., High-molecular-weight Hyaluronan—a Valuable Tool in Testing the Antioxidative Activity of Amphiphilic Drugs Stobadine and Vinpocetine, Journal of Pharm. Biomed. Anal., 1997, 419-424, 16.
Osmitrol (generic name Mannitol), Official FDA Information, side effects and uses, http://www.drugs.com/pro/osmitrol.html, 2010, 10 Pages.
Palmon, Sally et al, The Effect of Needle Gauge and Lidocaine pH on Pain During Intradermal Injection, Anesth Analg, 1998, 379-381, 86.
Park, et al., Biological Characterization of EDC-Crosslinked Collagen-Hyaluronic Acid Matrix in Dermal Tissue Restoration, Biomaterials, 2003, 1631-1641, 24, Elsevier.
Park, et al., Characterization of Porous Collagen/Hyaluronic Acid Scaffold Modified by 1-Ethyl-3-(3-Dimethylaminopropyl) Carbodiimide Cross-Linking, Biomaterials, 2002, 1205-1212, 23, Elsevier.
Phenylephrine. Open Drug Data and Drug Target Database 2013; http://www.drugbank.ca/drugsIDB00388. Accessed May 6, 2013.
Powell, Michael, Stability of Lidocaine in Aqueous Solution: Effect of Temperature, pH, Buffer, and Metal Ions on Amide Hydrolysis, Pharmaceutical Research, 1987, 42-45, 4 (1).
Prestwich, Glenn, Evaluating Drug Efficacy and Toxicology in Three Dimensions: Using Synthetic Extracellular Matrices in Drug Discovery, Accounts of Chemical Research, Jan. 2008, 139-148, 41(1).

(56) References Cited

OTHER PUBLICATIONS

Rehakova, Milena et al., Properties of Collagen and Hyaluronic Acid Composite Materials and Their Modification By Chemical Crosslinking, Journal of Biomedical Materials Research, 1996, 369-372, 30, US.
Remington's Pharmaceutical Sciences, 1980, 16th Edition, Mack Publishing Company, Easton, Pennsylvania.
Romero-Sandoval, Alfonso et al, Clonidine Reduces Hypersensitivity and Alters the Balance of Pro- and Anti-Inflammatory Leukocytes After Local Injection at the Site of Inflammatory Neuritis, Brain Behav Immun, Jul. 2007, 569-580, 21(5).
Rosenblatt, J. et al., Chain Rigidity and Diffusional Release in Biopolymer Gels, Controlled Release Society, 1993, 264-265, 20.
Rosenblatt, J. et al., The Effect of Collagen Fiber Size Distribution on the Release Rate of Proteins From Collagen Matrices by Diffusion, J Controlled Release, 1989, 195-203, 9, Elsevier Science Publishers B.V.
Sannino, A. et al., Crosslinking of Cellulose Derivatives and Hyaluronic Acid With Water-Soluble Carbodiimide, Polymer, 2005, 11206-11212, 46.
SCULPTRA® Aesthetic (injectable poly-L-lactic acid) Directions for Use, Product Insert, Jul. 2009, 12 Pages, Dermik Laboratories.
Segall, A.I. et al, Stability of Vitamin C Derivatives in Topical Formulations Containing Lipoic Acid, Vitamins A and E, International Journal of Cosmetic Science, 2008, 453-458, 30.
Segura, Tatiana et al., Crosslinked Hyaluronic Acid Hydrogels: A Strategy to Functionalize and Pattern, Biomaterials, 2005, 359-371, 26 (4).
Selvi, Enrico et al., Arthritis Induced by Corticosteroid Crystals, The Journal of Rheumatology, 2004, 622, 31 (3).
Serban, et al., Modular Extracellular Matrices: Solutions for the Puzzle, Methods, 2008, 93-98, 45 (1).
Shoroghi, Mehrdad et al, Effect of Different Epinephrine Concentrations on Local Bleeding and Hemodynamics During Dermatologic Surgery, Acta Dermatovenerol Croat, 2008, 209-214, 16(4).
Shu, et al., In Situ Crosslinkable Hyaluronan Hydrogels for Tissue Engineering, Biomaterials, 2004, 1339-1348, 25, Elsevier.
Shu, Xiao et al, Synthesis and evaluation of injectable, in situ crosslinkable synthetic extracellular matrices for tissue engineering, Journal of Biomedical Materials Research, 2006, 902-912, 79A.
Silver, Frederick et al., Physical Properties of Hyaluronic Acid and Hydroxypropylmethylcellulose in Solution: Evaluation of Coating Ability, Journal of Applied Biomaterials, 1994, 89-98, 5.
Skardal, Aleksander et al., Bioprinting Vessel-Like Constructs Using Hyaluronan Hydrogels Crosslinked With Tetrahedral Polyethylene Glycol Tetracrylates, Biomaterials, 2010, 6173-6181, 31.
Smith, Kevin et al., Five Percent Lidocaine Cream Applied Simultaneously to the Skin and Mucosa of the Lips Creates Excellent Anesthesia for Filler Injections, Dermatol Surg, 2005, 1635-1637, 31.
Tezel, Ahmet et al., The science of hyaluronic acid dermal fillers, Journal of Cosmetic and Laser Therapy, 2008, 35-42, 10.
Visiol, TRB Chemedica Ophthalmic Line, Product Info, May 2014, p. 1-2, Geneva, CH.
Visiol, Viscoelstic Gel for Use in Ocular Surgery, http://www.trbchemedica.com/index.php/option=com_content&tas, 2010, 1 Page.
Vivawoman, Sodium Ascorbyl Phosphate: A Stable Vitamin C, Nov. 3, 2010, 13 Pages, http://www.vivawoman.net/2010/11/sodium-ascrobyl-phosphate-a-stable-vitamin-c/.
Wahl, Gregor, European Evaluation of a New Hyaluronic Acid Filler Incorporating Lidocaine, Journal of Cosmetic Dermatology, 2008, 298-303, 7.
Waraszkiewicz, Sigmund et al., Stability-Indicating High-Performance Liquid Chromatographic Analysis of Lidocaine Hydrochloride and Lidocaine Hydrochloride with Epinephrine Injectable Solutions, Journal of Pharmaceutical Sciences, 1981, 1215-1218, 70 (11).
Weidmann, Michael, New Hyaluronic Acid Filler for Subdermal and Long-lasting Volume Restoration of the Face, European Dermatology, 2009, 65-68.
Xia, Yun et al., Comparison of Effects of Lidocaine Hydrochloride, Buffered Lidocaine, Diphenhydramine, and Normal Saline After Intradermal Injection, Journal of Clinical Anesthesia, 2002, 339-343, 14.
Yeom, Junseok et al., Effect of Cross-Linking Reagents for Hyaluronic Acid Hydrogel Dermal Fillers on Tissue Augmentation and Regeneration, Bioconjugate Chemistry, 2010, 240-247, 21, American Chemical Society.
Yoshimura, Kotaro et al., Cell-Assisted Lipotransfer for Cosmetic Breast Augmentation: Supportive Use of Adipose-Derived Stem/Stromal Cells, Aesth. Plast. Surg., 2008, 48-55, 32.
Yui, Nobuhiko et al., Inflammation Responsive Degradation of Crosslinked Hyaluronic Acid Gels, Journal of Controlled Release, 1992, 105-116, 26.
Yui, Nobuhiko et al., Photo-Responsive Degradation of Heterogeneous Hydrogels Comprising Crosslinked Hyaluronic Acid and Lipid Microspheres for Temporal Drug Delivery, Journal of Controlled Release, 1993, 141-145, 26.
Yun, Yang H. et al., Hyaluronan Microspheres for Sustained Gene Delivery and Site-Specific Targeting, Biomaterials, 2004, 147-157, 25, US.
Zulian, F. et al., Triamcinolone Acetonide and Hexacetonide Intra-Articular Treatment of Symmetrical Joints in Juvenile Idiopathic Arthritis: A Double-Blind Trial, Rheumatology, 2004, 1288-1291, 43.
Pierre, et al., "Basics of Dermal Filler Rheology," Dermatol Surg, 2015, vol. 41, pp. S120-S126.
Juvederm Volux, Product Insert, Jul. 26, 2018, 65 pages.
Boulle et al., "Lip Augmentation and Contour Correction with a Ribose Cross-linked Collagen Dermal Filler," Journal of Drugs in Dermatology, Mar. 2009, vol. 8, Issue 3, 8 pages.
Calderon et al., "Type II Collagen-Hyaluronan Hydrogel—A Step Towards a Scaffold for Intervertebral Disc Tissue Engineering," European Cells and Materials, 2010, vol. 20, pp. 134-148.
Crosslinking Technical Handbook, Termo Scientific, Apr. 2009, pp. 1-48.
Davidenko et al., "Collagen-hyaluronic acid scaffolds for adipose tissue engineering," Acta Biomaterialia, 2010, vol. 8, pp. 3957-3968.
Gomis et al., "Effects of Different Molecular Weight Elastoviscous Hyaluronan Solutions on Articular Nociceptive Afferents," Arthritis and Rheumatism, Jan. 2004, vol. 50, No. 1, pp. 314-326.
Kim et al., "Gallotannin Isolated from Euphorbia Species, 1, 2, 6-Tri-O-galloyl-b-D-allose, Decreases Nitric Oxide Production through Inhibition of Nuclear Factor-K>B and Downstream Inducible Nitric Oxide Synthase Expression in Macrophages," Jun. 2009, Biological and Pharmaceutical Bulletin, vol. 32, No. 6, pp. 1053-1056.
Nadim et al., "Improvement of polyphenol properties upon glucosylation in a UV-induced skin cell ageing model," International Journal of Cosmetic Science, Sep. 2014, vol. 36, No. 6, pp. 579-587.
Gallic Acid, National Center for Biotechnology Information, PubChem Compound Database, CID=370, 2018, https://pubchem.ncbi.nim.nih.gov/compound/370, 1 page.
Caffeic Acid, National Center for Biotechnology Information, PubChem Compound Database, CID=689043, 2018, https://pubchem.ncbi.nim.nih.gov/compound/689043, 1 page.
Park et al., "In vitro evaluation of conjugated Hyaluronic acid with Ascorbic Acid," Journal of Bone and Joint Surgery, British vol. 92-B, 2010, 1 page abstract.
Tomihata et al., "Crosslinking of Hyaluronic Acid with Water-Soluable Carbodiimide," J. Biomed Mater Res, Feb. 1997, vol. 37, No. 2, pp. 243-251.
Wang et al., "Development of hyaluronic acid-based scaffolds for brain tissue engineering," Acta Biomaterialia, 2009, pp. 2371-2384.

\* cited by examiner

HEAT STABLE HYALURONIC ACID COMPOSITIONS FOR DERMATOLOGICAL USE

CROSS REFERENCE

This application is a continuation of U.S. patent application Ser. No. 15/825,465 filed on Nov. 29, 2017, which is a continuation of Ser. No. 15/099,016 filed on Apr. 14, 2016, which granted as U.S. Pat. No. 9,855,367 on Jun. 2, 2018, which is a continuation of U.S. patent application Ser. No. 13/675,993 filed Nov. 13, 2012, which granted as U.S. Pat. No. 9,333,160 on May 10, 2016, which is a continuation of U.S. patent application Ser. No. 12/714,377 filed Feb. 26, 2010, which is abandoned, which is a continuation-in-part of U.S. patent application Ser. No. 12/687,048 filed Jan. 13, 2010, which is abandoned, the entire content of each of which is incorporated herein by reference.

BACKGROUND

Skin aging is a progressive phenomenon, occurs over time and can be affected by lifestyle factors, such as alcohol consumption, tobacco and sun exposure. Aging of the facial skin can be characterized by atrophy, slackening, and fattening. Atrophy corresponds to a massive reduction of the thickness of skin tissue. Slackening of the subcutaneous tissues leads to an excess of skin and ptosis and leads to the appearance of drooping cheeks and eye lids. Fattening refers to an increase in excess weight by swelling of the bottom of the face and neck. These changes are typically associated with dryness, loss of elasticity, and rough texture.

A variety of compounds can have an effect on the skin such as wrinkle reduction, antioxidant, haemostatic, vasoconstriction, anti-itching, anti-inflammatory and anti-irritant effects. For example, various vitamins as well and hyaluronic acid (HA) are known to have an effect on skin. Vitamin C is the L-enantiomer of ascorbate and has a well-described role in collagen development. Vitamin C is involved in the hydroxylation of collagen, which allows it to assume its triple-helix structure. Vitamin C is also known for its antioxidant effects and is well tolerated. HA is a natural polysaccharide. It is a polymer of disaccharides that are themselves composed of D-glucuronic acid and N-acetylglucosamine, linked to one another by alternating beta-1,4 and beta-1,3 glycosidic linkages. The polymers of this recurring unit may be from $10^2$ and $10^4$ kilo Daltons (kDa) in size, in vivo. Hyaluronic acid represents a natural constituent of the dermis, where it plays an important role in the hydration and elasticity of skin. There is a strong correlation between the water content in the skin and levels of HA in the dermal tissue. As skin ages, the amount and quality of HA in the skin is reduced. These changes lead to drying and wrinkling of the skin.

The use of HA in cosmetic and dermatological applications is known. HA is tolerated well and there is no immunogenicity associated with its use. The low incidence of side effects has lead to the use of HA for the treatment of wrinkles, fine lines, and scars. HA is subject to degradation through different pathways (e.g. enzymatic, temperature, free radicals), and therefore, its longevity in vivo is limited.

Disclosures of HA, vitamin C, and C-glycosides include U.S. patent application Ser. No. 12/393,884; U.S. Pat. No. 6,921,819 (a process for cross-linking solid hyaluronic acid (HA) by reacting it with a polyfunctional linker during hydration of the HA); U.S. Pat. No. 6,685,963 (acrylic particles of HA); U.S. publication 2006/0194758 (a method for making a hydrogel by cross linking high and low molecular weight sodium HAs); U.S. publication 2009/0036403 (cross-linking HA with a tetra functional PEG epoxide to provide "tunably" cross-linked HA); U.S. publication 2009/0143331 (a HA dermal filler with a degradation inhibitor, such as chondroitin sulphate, in order to provide a longer lasting filler); U.S. publication 2009/0143348 (HA combined with a steroid); and U.S. publication 2009/0155314 (HA combined with a botulinum toxin). Additionally, U.S. publications 2009/0148527, 2009/0093755, and 2009/0022808 disclose HA in microspheres, cross-linked with collagen, and coated with a protein, respectively. Further disclosures of HA include: WO 2009/034559 (a process for aesthetic and/or reparative treatment of the skin with compositions that contain at least one C-glycoside derivative); WO 2009/024719 (cosmetic and pharmaceutical compositions that contain HA and a C-glycoside derivative useful for filling recesses/depressions in the skin, restore volume of the body or the face, and to reduce the sign of aging); WO 2007/128923 (a method for preparing a biocompatible gel with controlled release of one or more active lipophilic and/or amphiphilic ingredients); U.S. publication 2009/0018102 (compositions containing HA and at least one retinoid or salt/derivative thereof in combination with an oligosaccharide and a HA degradation inhibitor, to treat wrinkles, lines fibroblast depletions and scars); U.S. Pat. No. 3,763,009 (a process for improving the oxidation resistance of ascorbic acid by subjecting a mixture of ascorbic acid, maltose and/or oligosaccharides to an enzyme derived from genera *Aspergillus, Penicillium* or others to enzymatically convert the mixture into ascorbic acid glucoside); U.S. Pat. No. 5,616,611 (a α-Glycosyl-L-ascorbic acid that exhibits no direct reducing activity, is stable, and is useful as a stabilizer, quality-improving agent, antioxidant, physiologically active agent, a UV-absorbant in pharmaceutical and cosmetic industries); U.S. Pat. No. 5,843,907 (the production and use of a crystalline 2-O-α-D-glucopyranosyl-L-ascorbic acid suitable for vitamin C enriching agents, food stuffs, pharmaceuticals, and cosmetics); and EP 0539196 (an industrial scale preparation of high purity 2-O-α-D-glucopyranosyl-L-ascorbic acid) and US publication 2002/0151711. Commercial products incorporating HA and/or vitamin C agents include: MESOGLOW® products, REVITACARE®, and NCTF® 135/135HA Mesotherapy products. Each of the above-cited references and printed publications are individually incorporated herein by reference in their entirety.

SUMMARY

Our invention includes a stable dermal filler formulation comprising a hyaluronic acid (HA) and at least one additional ingredient selected from the group consisting of a wrinkle reduction, antioxidant, haemostatic, vasoconstriction, anti-itching, anti-inflammatory and anti-irritant ingredient. Stability of the dermal filler formulation can be determined by subjecting the dermal filler formulation to a heat treatment selected from the group consisting of (a) steam sterilization (equivalently "autoclaving") and (b) about 32 days at about 45° C., with substantial retention after the heat treatment of one or more of the dermal filler characteristics of being clear, homogenous, and cohesive, and without substantial degradation of the dermal filler formulation after the heat treatment. Preferably the steam sterilization is carried out at a temperature of at least about 120° C., as we have found that a high temperature steam sterilization reduces the sterilization time required while still providing all sterility requirements, without degradation of the dermal filler formulation occurring when the additional ingredients set forth herein are present in the formulation. More preferably, the steam sterilization is carried out at a temperature between about 130° C. and 135° C., because we found that such a particular high temperature steam sterilization not only further reduces the sterilization time required while still providing all sterility requirements but as well can be carried out with little or no degradation of the dermal filler formulation occurring. Preferably, the steam sterilization is carried out for between about one minute and about 10 minutes and more preferably for between about 1 minute and about 5 minutes.

Our invention also includes a steam sterilization stable dermal filler formulation comprising a hyaluronic acid (HA) and at least one additional ingredient selected from the group consisting of wrinkle reduction, antioxidant, haemostatic, vasoconstriction, anti-itching, anti-inflammatory and anti-irritant ingredients, wherein the formulation is substantially clear (i.e. little or no modification of the pre-heat [i.e. steam] treatment dermal filler formulation color occurs as compared to the color of the post heat treatment dermal filler formulation), homogenous, cohesive stable and not substantially degraded after steam sterilization. Degradation can be shown after steam sterilization by, for example, discoloration of the steam sterilized dermal filler formation and/or by a decrease in the homogeneity of the formulation or in other formulation rheological properties. Substantially clear means that on visual inspection the dermal filler formulation both before and after steam sterilization is not opaque. Substantially homogenous means the dermal filler formulation both before and after steam sterilization has the same consistency (eg well mixed throughout). Substantially monophasic means the dermal filler formulation both before and after steam sterilization comprises only one phase, meaning it is a gel with no particles. Substantially cohesive means the ability of the dermal filler formulation both before and after steam sterilization to retain its shape and resist deformation. Cohesiveness is affected by, among other factors, the molecular weight ratio of the initial free HA, the degree of crosslinking, the amount of residual free HA following crosslinking, and the pH of the dermal filler formulation. Moreover, a cohesive dermal filler formulation resists phase separation when tested according to the method disclosed by Example 1A herein.

Our dermal filler formulations are stable after steam sterilization (i.e. at a temperature between about 120° C. to 135° C. or greater). Additionally our dermal filler formulations have long term storage or shelf life stability as shown for example by maintenance of stability of the dermal filler formulations in an environment at about 45° C. for about 32 days (accelerated heat testing), which can be considered to show that stability will be maintained for about 1 to 3 years at room temperature; stability can be determined by substantial retention at room temperature of one or more of the dermal filler characteristics of being clear, homogenous, and cohesive, and without substantial degradation of the dermal filler formulation. Stability of our dermal filler formulations can be determined over a period of or about 25 days to about 35 days at a temperature of about 35° to 50° C. Preferably, as set forth above, the accelerated heat stability testing is carried out for about 32 days at about 45° C. Substantially stable after the accelerated heat (stability) testing carried out as set forth above, or substantially stable after autoclaving or after steam sterilization of the dermal filler formulation, means the dermal filler formulation retains (as being resistant to degradation) at least 80% and preferably at least 90% and most preferably at least about 95% of at least one of its measured characteristics of transparency, pH, extrusion force, rheological characteristics, hyaluronic acid (HA) concentration, sterility, osmolarity, and same additional ingredient concentration. In our dermal filler formulation the HA is preferably cross-linked and the HA can be present in an amount of about 1 to about 40 mg/mL.

An additional ingredient in our dermal filler formulation can be a vitamin B, C or E and the additional ingredient can be present in an amount of about 0.001% to about 10% w/w, and preferably be present in an amount of from about 0.1% to about 3% w/w. Important, the additional ingredient can provide the dermal filler formulation with improved rheological properties resulting in less extrusion force required for administration compared to an HA gel formulation without the additional constituent.

Our invention also includes a method for treating a dermal condition such as fine lines, wrinkles, fibroblast depletions, and/or scars of a patient by administering to the patient an effective amount of a steam sterilization stable dermal filler formulation comprising a hyaluronic acid (HA) and at least one additional ingredient selected from the group consisting of wrinkle reduction, antioxidant, haemostatic, vasoconstriction, anti-itching, anti-inflammatory and anti-irritant ingredients, wherein the formulation is clear, homogenous, cohesive, stable and not degraded after steam sterilization and wherein the appearance of the fine lines, wrinkles, fibroblast depletions, or scars is diminished. The administration can be by sub dermal, intra-dermal or subcutaneous injected (i.e. local injection administration) into a facial skin of the subject.

Our invention also includes a steam sterilization stable dermal filler formulation comprising a hyaluronic acid and at least one additional ingredient selected from the group consisting of AA2G and dexpanthenol, wherein the stability of the dermal filler formulation is significantly increased by the additional ingredient—as shown by the dermal filler formulation having a $\Delta$ Tan $\delta$ 1 Hz<−0.05.

DRAWINGS

DESCRIPTION

Figure 1:
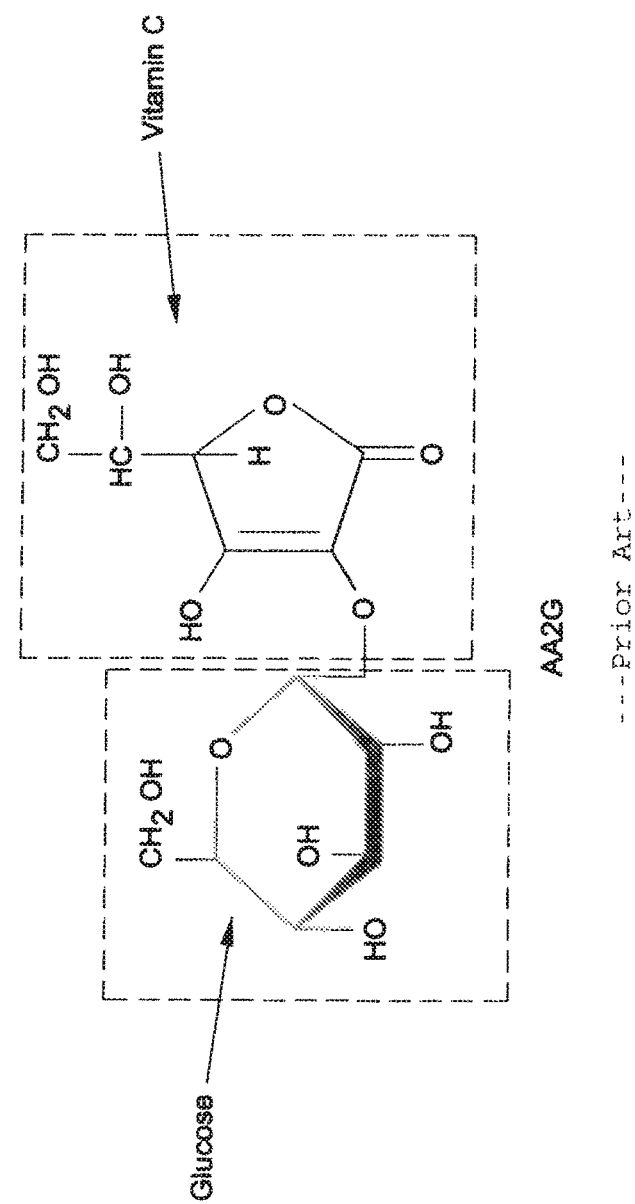
FIG. 1 is a representation of the structure of an ascorbyl-2-glucoside, also known as AA2G™ (Hayashibara Co., Japan).

Our invention is based on the discovery that a steam sterilization stable HA based dermal filler can be prepared with an additional ingredient (that is besides the HA present in the formation) which is a wrinkle reduction, antioxidant, haemostatic, vasoconstriction, anti-itching, anti-inflammatory and/or anti-irritant ingredient. An HA dermal filler within the scope of our invention ("the dermal filler formulation") is (autoclaving) steam sterilization stable and as demonstrated stability after about 32 days at about 45° C. The formulation does not exhibit any degradation as shown by the pre and post autoclaved formulations both being clear, homogenous, and cohesive.

The dermal filler formulation can also exhibit greater stability than an HA gel formulation without the additional constituent. Without wishing to be bound by theory it may be that the matrix of the cross-linked HA used in our formulation sequesters, renders non-reactive and thereby prevents the additional ingredient (as set forth for example in Examples 4-6, 10-11, 13, 15-16, 20, 24, and 25-29, supra) from degrading and causes degradation of the dermal filler formulation during steam sterilization. Additionally, the additional ingredient can be hydrophilic and provides protection to the HA from degradation during steam sterilization and/or after administration of the dermal filler formulation to a patient. Without wishing to be bound by theory, the incorporation of an additional ingredient in the dermal filler formulation may inhibit free-radical scavenging at the injection/implant site, thereby prolonging dermal filler duration after patient administration. After steam sterilization the additional ingredient can upon administration (as by subdermal injection) be released from the dermal filler formulation for cosmetic or therapeutic effect.

Autoclave stable or steam sterilization stable as used herein means a dermal filler formulation that is resistant to degradation such that the formulation retains at least one, and preferably all, of the following aspects after steam sterilization: transparent or clear appearance pH, extrusion force and/or rheological characteristics, hyaluronic acid (HA) concentration, osmolarity, and same additional ingredient concentration.

High molecular weight HA as used herein describes a HA material having a molecular weight of at least about 1.0 million Daltons (mw≥$10^6$ Da or 1 MDa) to about 4.0 MDa. For example, the high molecular weight HA in the present compositions may have a molecular weight of about 2.0 MDa. In another example, the high molecular weight HA may have a molecular weight of about 2.8 MDa.

Low molecular weight HA as used herein describes a HA material having a molecular weight of less than about 1.0 MDa. Low molecular weight HA can have a molecular weight of between about 200,000 Da (0.2 MDa) to less than about 1.0 MDa, for example, between about 300,000 Da (0.3 M Da) to about 750,000 Da. (0.75 MDa).

Degree of crosslinking as used herein refers to the intermolecular junctions joining the individual HA polymer molecules, or monomer chains, into a permanent structure, or as disclosed herein the soft tissue filler composition. Moreover, degree of crosslinking for purposes of the present disclosure is further defined as the percent weight ratio of the crosslinking agent to HA-monomeric units within the cross-linked portion of the HA based composition. It is measured by the weight ratio of HA monomers to crosslinker (HA monomers:crosslinker).

Free HA as used herein refers to individual HA polymer molecules that are not crosslinked to, or very lightly crosslinked to (very low degree of crosslinking) the highly crosslinked (higher degree of crosslinking) macromolecular structure making up the soft tissue filler composition. Free HA generally remains water soluble. Free HA can alternatively be defined as the "uncrosslinked," or lightly cross-linked component of the macromolecular structure making up the soft tissue filler composition disclosed herein.

The presence of an additional ingredient in the dermal filler formulation can provide a stability and longevity that is not exhibited in a dermal filler formulation containing HA without the additional ingredient. The disclosed formulations after steam sterilization are homogenous, uncolored, clear, cohesive gel. Our invention includes methods for treating dermatological conditions, such as fine lines, wrinkles, fibroblast depletions, and/or scars afflicting a subject by administering to a patient an effective amount of the dermal filler formulation. The patient can be any mammal, preferably a human of any age, gender or race. Although typically a subject experiencing the signs of aging skin is an adult, subjects experiencing premature aging or other skin conditions suitable for treatment (for example, a scar) with the HA gel formulation can be treated as well.

Our dermal filler formulation comprise HA which is preferably at least partly cross-linked and can contain some not cross-linked HA. Although any pharmaceutically or cosmetically acceptable HA can be used in the disclosed compositions and formulations, in certain embodiments, the preferred HA utilized includes those sold as JUVEDERM®, JUVEDERM® 30, JUVEDERM® Ultra Plus, JUVEDERM® Ultra injectable gel (Allergan Inc, Irvine, Calif.). In certain embodiments, the formulation comprises a HA gel matrix and an additional constituent. HA is a known hydrogel. The gel can be injectable, bioresorbable, monophasic, or biphasic. In some embodiments, the additional constituent can be directly incorporated into the HA gel. In other embodiments, in order to increase affinity with the medium or increase stability, modification of the molecule by derivatization or encapsulation of the constituent can be performed, as described above. For instance, certain oily molecules cannot be introduced directly into a hydrophilic matrix, and lead to a heterogeneous product. Derivatization of the molecule by grafting hydrophilic moieties is required to increase homogeneity of the gel. In some embodiments, the gel composition can include a biocompatible or biodegradable vessel.

The HA gel can be made by any known, suitable methods. Cross-linked HA gels typically have high viscosity and require considerable force to extrude through a fine needle. Uncross-linked HA is often used as a lubricant to facilitate the extrusion process. However, especially in HA dermal fillers and implants, uncross-linked HA does not contribute to the persistence of the final product in vivo. The formulations exhibit increased stability compared to formulations containing HA without the additional constituent. Stability is determined by assessing the homogeneity, color, and clarity, pH, and rheological properties of the gel formulation. The formulations disclosed herein are considered stable if they remain homogenous, colorless, and/or clear, and exhibit stable pH and rheology. The disclosed formulations remain stable for at least about 6 months, at least about 1 year, at least about 2 years or at least about 3 years.

A cross-linking agent can be used to cross-link the HA according to the present disclosure. The cross-linking agent may be any agent known to be suitable for cross-linking HA and its derivatives via hydroxyl groups. Suitable cross-linking agents include but are not limited to, 1,4-butanediol diglycidyl ether, 1,4-bis(2,3-epoxypropoxy)butane, and/or 1,4-bisglycidyloxybutane (commonly known as BDDE), 1,2-bis(2,3-epoxypropoxy)ethylene, and 1-(2,3-epoxypropyl)-2,3-epoxycyclohexane. The use of more than one crosslinking agent or a different cross-linking agent is included from the scope of the present disclosure.

Dermal fillers can be used to treat moderate to severe facial wrinkles and folds such as nasolabial folds (those lines that extend from the nose to the corners of the mouth). In one embodiment, a dermal filler can be a gel implant formulation that includes HA and an additional constituent. The formulations disclosed herein can further include additional cosmetic agents that supplement and improve the appearance of skin. The cosmetic active ingredients may include, but are not limited to, antioxidants, vitamins, tension agents, and moisturizers.

The formulations disclosed herein can be injected with a syringe into the mid to deep dermis of the face. The dermis is the subsurface skin layer that contains connective tissue, nerve endings, and blood vessels. The formulations, when administered as dermal fillers can improve skin appearance by lifting and adding volume to the wrinkles and folds in the treatment area. Further, in certain embodiments, improvement can be seen due to increased collagen production that results from administration of the formulation.

As used herein, "cosmetic" is an adjective referring to improving the appearance of a surface or covering defects. Typically, cosmetic compositions can be used to improve aesthetic rather than functional aspects of a surface. Most commonly, cosmetic compositions are formulated for application as a health and beauty treatment or for affecting personal appearance of the body, for example, keratinous surfaces such as skin, hair, nails, and the like.

As used herein, "formulation" and "composition" may be used interchangeably and refer to a combination of elements that is presented together for a given purpose. Such terms are well known to those of ordinary skill in the art.

Examples of additional ingredients (agents) which can be included in the present dermal filler formulations are anti-itch, anti-cellulite, anti-scarring, and anti-inflammatory agents, anesthetics, anti-irritants, vasoconstrictors, vasodilators, as well as agents to prevent/stop bleeding, and improve/remove pigmentation, moisturizers, desquamating agents, tensioning agents, anti-acne agents. Anti-itch agents can include methyl sulphonyl methane, sodium bicarbonate, calamine, allantoin, kaolin, peppermint, tea tree oil, camphor, menthol, hydrocortisone and combinations thereof. Anti-cellulite agents can include forskolin, xanthine compounds such as, but not limited to, caffeine, theophylline, theobromine, and aminophylline, and combinations thereof. Anesthetic agents can include lidocaine, benzocaine, butamben, dibucaine, oxybuprocaine, pramoxine, proparacaine, proxymetacaine, tetracaine, and combinations thereof. Anti-scarring agents can include IFN-.gamma., fluorouracil, poly (lactic-co-glycolic acid), methylated polyethylene glycol, polylactic acid, polyethylene glycol and combinations thereof. Anti-inflammatory agents can include dexamethasone, prednisolone, corticosterone, budesonide, estrogen, sulfasalazine, mesalamine, cetirizine, diphenhydramine, antipyrine, methyl salicylate, loratadine, and derivatives and combinations thereof. Additionally, active agents such as epinephrine, thymidine, cytidine, uridine, antiypyrin, aminocaproic acid, tranexamic acid, eucalyptol, allantoin, glycerin, and sodium selenite, can be included. The disclosed dermal filler formulations can further comprise degradation inhibitors. Degradation inhibitors, include but are not limited to, glycosaminoglycans (e.g., heparin, heparin sulfate, dermatan sulfate, chondroitin sulfate, o-sulfated HA, linamarin, glucosamine, and amygdalin), antioxidants (e.g. ascorbic acid, melatonin, vitamin C, vitamin E, sodium selenite, glutathion, retinoic acid, coenzyme, beta-carotene, allopurinol, mannitol, caffeic acid, caffeine, polyphenol, theobromine, catechin), proteins (e.g., serum hyaluronidase inhibitor), and fatty acids (e.g. saturated $C_{10}$ to $C_{22}$ fatty acids), vitamin B and complex, and combinations thereof as noted, in certain embodiments, the additional ingredient can be an antioxidant. In certain embodiments, the antioxidant comprises a vitamin C such as ascorbyl-2-glucoside (available as AA2G™, Hayashibara Co., Japan) (FIG. 1), and/or a vitamin E such as d-alpha-tocopheryl polyethylene glycol 1000 succinate (TPGS). Anti-irritants can include thymol, bisabolol. Healing agents can include allantoin, eucalyptol, chitosane, cytidine, thimidine, uridine, lanoline. Anti-bleeding: epinephrine, norepinephrine, phenylephrine, synephrine, naphazoline, aminocaproic acid, tranexamic acid, ethamsylate, vitamin K. Collagen promoters can include retinol, peptide sequences. Additionally, active ingredients (agents) such as epinephrine, thymidine, cytidine, uridine, antipyrine, aminocaproic acid, eucalyptol, sodium selenite, can be included.

In some embodiments, the HA is present at a concentration of about 1 to about 40 mg/mL, or about 10 to about 40 mg/mL, or about 20 to about 30 mg/mL. In certain embodiments, the HA is present in a concentration of about 20 to about 25 mg/mL. In certain embodiments, the HA is present at a concentration of 24 mg/mL. The additional constituent can be present in an amount of about 0.001 to about 10% w/w, or from about 0.001 to about 5% w/w, or from 0.3 to about 3% w/w.

In certain embodiments, the disclosure provides a dermal filler comprising (a) about 90 wt %, or about 95 wt %, or about 100 wt % of a high molecular weight (about 1 million to about 3 million Daltons) HA; and (b) 0 wt %, or about 5 wt %, or about 10 wt % of a low molecular weight (less than 1 million Daltons) HA. In certain embodiments, the HA is present in the dermal filler at a concentration of about 10 to about 24 mg HA/mL dermal filler and the HA is about 4% to about 11% cross-linked. In certain embodiments, the cross linker is 4-butane diol diglycidyl ether (BDDE). The dermal filler can further comprise about 0.1 wt % or 0.6 wt %, or 1.0 wt % of an ascorbyl-2-glucoside, such as AA2G™ (Hayashibara, Japan). In a preferred embodiment, 0.6 wt % AA2G™ (i.e., 6 mg AA2G™/g HA) is utilized and renders a concentration of 2.1012 mM AA2G™.

Topical formulations of AA2G™ are known. However, there are no subdermally administered formulations of AA2G™ available, which is likely due to the fact that a topical AA2G™ is not thought to lend itself to an injectable formulation. The disclosure provides the first injectable formulation of AA2G™ that is efficacious, compatible, and stable over time.

The disclosed compositions are also well suited for mesotherapy. Mesotherapy is a non-surgical cosmetic treatment technique involving intra-epidermal, intra-dermal, and/or subcutaneous injection of an agent (micronutrients, vitamins, mineral salts, etc). The compositions are administered in the form of small multiple droplets into the epidermis, dermo-epidermal junction, and/or the dermis.

The formulations of the disclosure can be injected utilizing needles with a diameter of about 0.26 to about 0.4 mm and a length ranging from about 4 to about 14 mm. Alternately, the needles can be 21 to 32 G and have a length of about 4 mm to about 70 mm. Preferably, the needle is a single-use needle. The needle can be combined with a syringe, catheter, and/or a pistol (for example, a hydropneumatic-compression pistol).

The formulations can be administered once or over several sessions with the subject spaced apart by a few days, or weeks. For instance, the subject can be administered a formulation every 1, 2, 3, 4, 5, 6, 7, days or every 1, 2, 3, or 4, weeks. The administration can be on a monthly or bi-monthly basis. Further, the formulation can be administered every 3, 6, 9, or 12 months.

Our dermal filler formulation can optionally include one or more agents such as, without limitation, emulsifying agents, wetting agents, sweetening or flavoring agents, tonicity adjusters, preservatives, buffers antioxidants and flavonoids. Tonicity adjustors useful in a pharmaceutical composition of the present disclosure include, but are not limited to, salts such as sodium acetate, sodium chloride, potassium chloride, mannitol or glycerin and other pharmaceutically acceptable tonicity adjusters. Preservatives useful in the dermal filler formulation described herein include, without limitation, benzalkonium chloride, chlorobutanol, thimerosal, phenyl mercuric acetate, and phenyl mercuric nitrate. Various buffers and means for adjusting pH can be used to prepare the dermal filler formulation, including but not limited to, acetate buffers, citrate buffers, phosphate buffers and borate buffers. Similarly, antioxidants useful in the dermal filler formulation include for example, sodium metabisulfite, sodium thiosulfate, acetylcysteine, butylated hydroxyanisole and butylated hydroxytoluene. Flavonoids are compounds found in plants that are well known to have diverse beneficial biochemical and antioxidant effects. Subcategories of flavonoids include: flavones, flavonols, flavanones and flavanonols. Examples of flavonoids include: luteolin, apigenin, tangeritin, quercetin, kaempferol, myricetin, fisetin, isorhamnetin, pachypodol, rhamnazin, hesperetin, naringenin, eriodictyol, homoeriodictyol, taxifolin, dihydroquercetin, dihydrokaempferol, tannic acid, tannins, condensed tannins, and hydrolysable tannins. It is understood that these and other substances known in the art can be included in the dermal filler formulations disclosed herein. The pH of the disclosed dermal filler formulations can be about 5.0 to about 8.0, or about 6.5 to about 7.5. In certain embodiments, the pH of the formulation is about 7.0 to about 7.4 or about 7.1 to about 7.3.

A dermal filler formulation must be capable of withstanding sterilization which is a strict requirement before the product can be sold (the product must be sterile). Sterilization can be carried out by steam sterilization, filtration, microfiltration, gamma radiation, ETO light or by a combination of these methods. It is known that a dermal filler can be steam sterilized (autoclaved) without degradation of physical properties, but when a dermal filler formulation contains an additional labile ingredient (such as an antioxidant, wrinkle reduction, haemostatic, vasoconstriction, anti-itching, anti-inflammatory, and/or anti-irritant ingredient, such as a vitamin, vitamin derivative or analgesic compound) the entire dermal filler formulation or at least the additional (heat labile) ingredient is sterilized by a non-heat treatment such as by a filtration sterilization method. Thus, the known dermal filler product ("Revitacare") is sold in two separate vials or containers, one vial containing the HA (which is autoclave sterilized)) and the second vial containing any additional ingredients (the second vial contents are sterilized by filtration). Another known dermal filler product NCTF®135 HA is sold in a single container holding both HA and any additional ingredients, all having been sterilized by microfiltration. It is an important aspect of our invention that we mix the HA and the additional ingredients and then autoclave the completed dermal filler formulation with maintenance of gel properties (i.e. non-degraded and storage stable formulation). Additionally we have discovered dermal filler formulations that exhibit retention of stability after being treated (accelerated heat test environment) to about 45° C. for about 30 days, or at least about 60 days, or at least about 90 days with no degradation of physical properties.

To reiterate an important aspect of our invention and a significant distinction over known dermal fillers is that our dermal filler formulations are prepared by: (1) mixing the HA and the additional ingredient(s), and then; (2) autoclaving (no filtration sterilization of any component) the complete dermal filler formulation with; (3) maintenance of the desired gel properties (no degradation of any dermal filler constituent or ingredient, and stable).

EXAMPLES

In the Examples below autoclaving means steam sterilization carried out at a temperature between about 130° C. to about 135° C. for between about one minute and about 10 minutes.

Example 1A

Method for Determining Gel Cohesivity

For purposes of example only and not to be considered as limiting the present invention in any way, the following tests may be performed in order to evidence or quantify cohesivity of a HA-based gel composition.

First, 0.2 g or 0.4 g of a gel composition to be tested is placed in a glass syringe. Next, 0.2 g or more of phosphate buffer is added to the syringe and the mixture is thoroughly mixed for about 1 hour to obtain a homogenous mixture. Then, the homogenized mixture is centrifuged for 5 min at 2000 tr/min to remove the air bubbles and to allow the decantation of any particles. The syringe is then held in a vertical position and one drop of eosin colorant is deposited at the surface of the gel by means of a syringe and an 18G needle. After 10 min, the dye has slowly diffused through the gel.

After dilution of the gel, homogenization and decantation, a relatively low cohesivity gel shows a phase separation (an upper diluted less viscous phase without particles and a lower one composed of decanted particles that are visible with the naked eye or under microscope). Under the same conditions, a highly cohesive gel shows substantially no phase separation, and the dye is prevented from diffusing into the cohesive formulation. A relatively less cohesive gel, on the other hand, shows a clear phase separation.

Example 1

Properties of Formulations of NaHA and Water Soluble Molecules are Tested

The active ingredient was incorporated into a NaHA matrix and autoclaved. The properties of the gel, aspect (i.e., color/clarity/homogeneity) and extrusion force were analyzed after sterilization at 3 years equivalent at room temperature. Table 1 shows that all formulations were clear, homogenous, and uncolored at the 3-year mark. The extrusion forces after autoclaving and at 3 years equivalent at room temperature are shown as well. In conclusion, the incorporation of the molecules has no impact on gel properties and ingredient structure.

TABLE 1

| Ingredient | Content (%) | Aspect | Extrusion force (N) after autoclaving | Extrusion force (N) 3 years~room T ° C. |
|---|---|---|---|---|
| Allantoin | 0.3 | Clear | PASSED | PASSED |
|  | 0.5 | Homogeneous | PASSED | PASSED |
| Cytidine | 0.5 | Uncolored | PASSED | PASSED |
|  | 1 |  | PASSED | PASSED |
| Thymidine | 0.5 |  | PASSED | PASSED |
|  | 1 |  | PASSED | PASSED |
| Uridine | 0.5 |  | PASSED | PASSED |
|  | 1 |  | PASSED | PASSED |
| Antipyrin | 0.5 |  | PASSED | PASSED |
|  | 1 |  | PASSED | PASSED |
| Aminocaproic acid | 0.5 |  | PASSED | PASSED |
|  | 1 |  | PASSED | PASSED |
| Tranexamic acid | 0.5 |  | PASSED | PASSED |
| Eucalyptol | 0.5 |  | PASSED | PASSED |
| Sodium selenite | 0.1 |  | PASSED | PASSED |
| Glycerin | 0.5 |  | PASSED | PASSED |

Acceptance criteria: "Passed" means that the change of extrusion force (ΔF) was less than two Newtons (<2 N). In other words the measured ΔF of the extrusion force of the HA gel with the specified ingredients minus the extrusion force of the HA gel without the added ingredients was <2 N.

Example 2

Preparation of NaHA Gel Containing Vitamin C

Ascorbic acid (1% w/w) was incorporated into a NaHA matrix. (JUVEDERM® FORMA). The pH was adjusted to about 7 and composition was autoclaved. The gel obtained was clear, yellow and degraded.

Example 3

Alternative Preparation of NAHA Gel Containing Vitamin C

Magnesium Ascorbyl Phosphate (MAP) (0.6%, 1 or 2% w/w) was incorporated in a NaHA matrix (JUVEDERM® Ultra). The pH was adjusted to about 7 and the compositions were autoclaved. All gels obtained were uncolored and clear. The gel properties after autoclaving are shown in Table 2. Extrusion force acceptance criteria: Conform with NaHA matrix specifications.

TABLE 2

| Formulation | After autoclaving Extrusion force (N) |
|---|---|
| JUVEDERM ® Ultra + 0.6% MAP | PASSED |
| JUVEDERM ® Ultra + 1% MAP | PASSED |
| JUVEDERM ® Ultra + 2% MAP | PASSED |

Rheology data of the gel containing 2% MAP after autoclaving is shown in Table 3. Rheological properties are followed as a function of time using a controlled stress rheometer according to the following method: frequency sweep from 0.05 to 10 Hz with 0.8% controlled strain. A degradation of the gel was observed by rheology. TAN δxHZ is a rheological characterisation which shows the ratio of viscous modulus to elastic modulus. It shows the degradation of the gel.

Δ Tan δ1 Hz=(Tan δ1 Hz formulation)−(Tan δ1 Hz NaHA matrix)

Acceptance criterion: Δ Tan δ 1 Hz<0.1

TABLE 3

| Formulation | Δ Tan δ 1 Hz |
|---|---|
| JUVEDERM ® Ultra + 2% MAP | 0.344 |

Example 4

Alternative Preparation of NAHA Gel Containing Vitamin C

Sodium Ascorbyl Phosphate (SAP) (0.6%, 1% and 2% w/w) was incorporated in an NaHA matrix (JUVEDERM® Ultra). The pH was adjusted to about 7 and the composition was autoclaved. All gels obtained were uncolored and clear. The gel properties after autoclaving are shown in Table 4.

TABLE 4

| Formulation | After autoclaving Extrusion force (N) |
|---|---|
| JUVEDERM ® Ultra + 0.6% SAP | PASSED |
| JUVEDERM ® Ultra + 1% SAP | PASSED |
| JUVEDERM ® Ultra + 2% SAP | PASSED |

Rheology data of the gel containing 2% SAP after autoclaving is shown in Table 5. No degradation of the gel was observed by rheology.

TABLE 5

| Formulation | Δ Tan δ 1 Hz |
|---|---|
| JUVEDERM ® Ultra + 2% SAP | 0.089 |

Example 5

Alternative Preparation of NaHA Gel Containing Vitamin C

Ascorbic acid 2-Glucoside (AA2G™) at a concentration of 0.6%, 1% and 2% w/w was incorporated in an NaHA matrix (JUVEDERM® Ultra Plus). The pH was adjusted to about 7 and the composition was autoclaved. All gels obtained were uncolored and clear. The gel properties after autoclaving are shown in Table 6.

TABLE 6

| Formulation | After autoclaving Extrusion force (N) |
|---|---|
| JUVEDERM ® Ultra Plus + 0.6% AA-2G | PASSED |
| JUVEDERM ® Ultra Plus + 1% AA-2G | PASSED |
| JUVEDERM ® Ultra Plus + 2% AA-2G | PASSED |

The gels containing 0.6%, 1% and 2% were stable (pH, injection force) after autoclaving. Rheology data of the gels containing 0.6%, 1% and 2% w/w AA2G™ after autoclaving is shown in Table 7. No degradation of the gel was observed by rheology at each AA2G™ concentration.

TABLE 7

| Formulation | Δ Tan δ 1 Hz |
|---|---|
| JUVEDERM ® Ultra Plus + 0.6% AA2G ™ | −0.010 |
| JUVEDERM ® Ultra Plus + 1% AA2G ™ | −0.014 |
| JUVEDERM ® Ultra Plus + 2% AA2G ™ | −0.016 |

Rheological studies showed an slightly increase of the stability of the gel in the presence of the additive.

Example 6

Effect of Vitamin C on Aspect and Stability of the Gel

The shelf-life at 45° C. during 32 days was tested for the formulations prepared in example 5 and the NaHA matrix JUVEDERM® Ultra Plus. Rheology data of the gels containing 0.6%, 1% and 2% of AA2G™ are shown in Table 8.

TABLE 8

| Formulation | Δ Tan δ 1 Hz |
|---|---|
| JUVEDERM ® Ultra Plus + 0.6% AA2G ™ | −0.050 |
| JUVEDERM ® Ultra Plus + 1% AA2G ™ | −0.045 |
| JUVEDERM ® Ultra Plus + 2% AA2G ™ | −0.059 |

The gels containing ascorbyl glucoside maintained their properties after autoclaving and over a period of 32 days at 45° C. Surprising Rheological studies showed an increase of the stability of the gel in the presence of the additive.

Example 7

Preparation of NaHA Gel Containing Vitamin E

Tocopheryl Acetate (0.5% w/w) was incorporated into a NaHA matrix. (JUVEDERM® 30) and autoclaved. The gel obtained was unclear, white.

Example 8

Alternative Preparation of NaHA Gel Containing Vitamin E

Sodium Tocopheryl Phosphate (STP), at 0.4%, 1.2% w/w, was incorporated in a NaHA matrix (JUVEDERM® FORMA) and autoclaved. The gel obtained was not clear (white).

Example 9

Alternative Preparation of NaHA Gel Containing Vitamin E

Polyoxyethanyl-α-tocopheryl sebacate (0.7% w/w) was incorporated in a NaHA matrix (JUVEDERM® Ultra Plus) and autoclaved. The gel obtained was clear, but heterogenous.

Example 10

Alternative Preparation of NaHA Gel Containing Vitamin E

Tocopherol polyethylene glycol 1000 succinate (TPGS) was incorporated in varying concentrations (1%, 3.5% and 7% w/w) in a NAHA matrix (JUVEDERM® FORMA) and autoclaved. "JUVEDERM® FORMA" means the Juvederm formulation was used. All gels obtained were uncolored and clear. The gel properties after autoclaving are shown in Table 9.

TABLE 9

| Formulation | Extrusion force (N) |
|---|---|
| JUVEDERM ® FORMA + 1% TPGS | PASSED |
| JUVEDERM ® FORMA + 3.5% TPGS | PASSED |
| JUVEDERM ® FORMA + 7% TPGS | PASSED |

Rheology data of the gels containing 1%, 3.5% and 7% TPGS after autoclaving is shown in Table 10. No degradation of the gel was observed by rheology at each TPGS concentration.

TABLE 10

| Formulation | Δ Tan δ 1 Hz |
|---|---|
| JUVEDERM ® FORMA + 1% TPGS | 0.008 |
| JUVEDERM ® FORMA + 3.5% TPGS | −0.007 |
| JUVEDERM ® FORMA + 7% TPGS | −0.011 |

These rheological studies showed the stability of the dermal filler formulation with a particular additional ingredient.

Example 11

Stability of Formulations Containing Additional Ingredients

Figure 3:
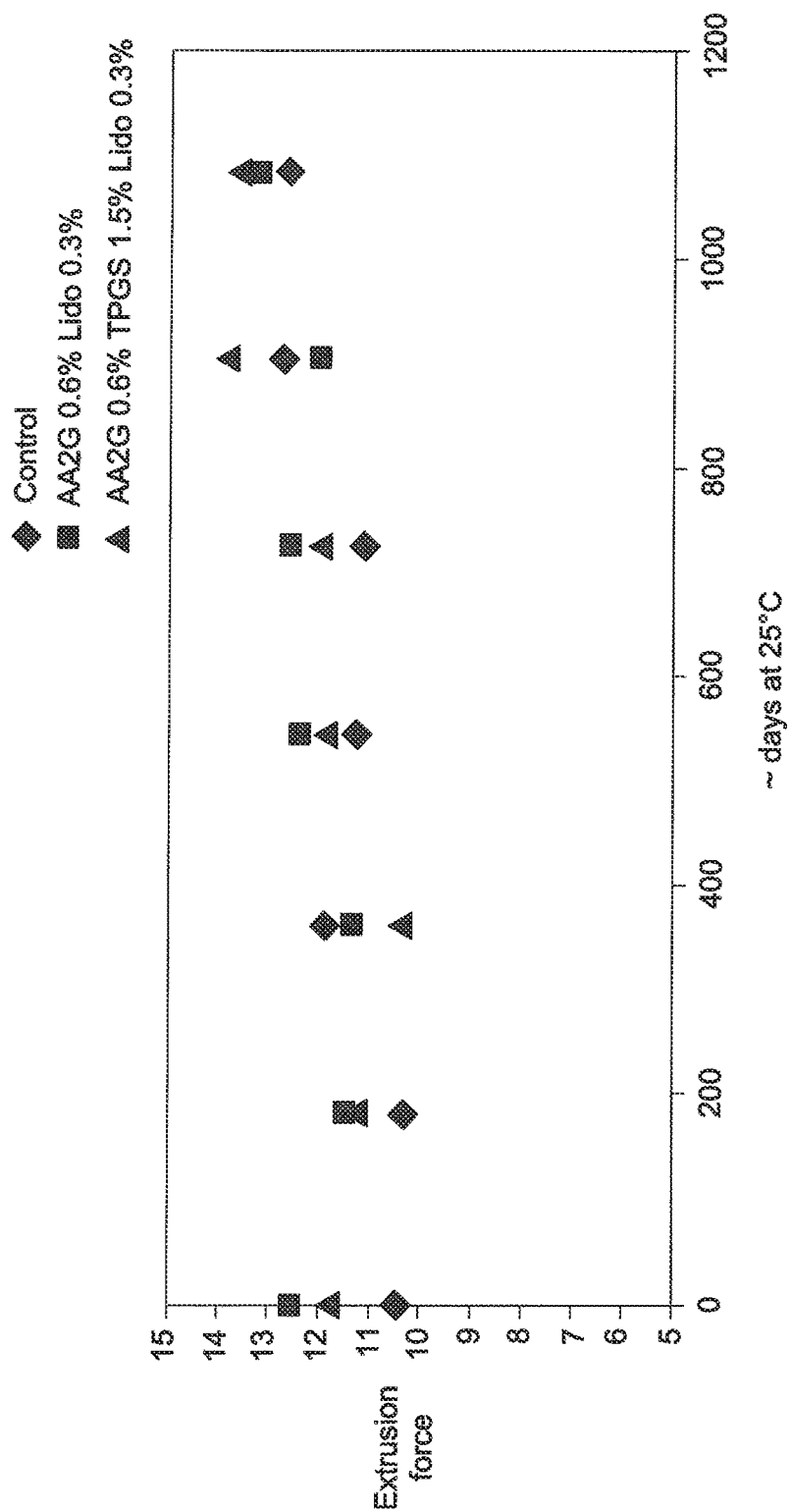
FIG. 3 is a graph showing the extrusion force over time (3 yr equivalent at 25° C.) in compositions: control, AA2G™ plus lidocaine, and AA2G™ plus lidocaine and TPGS.
Figure 4:
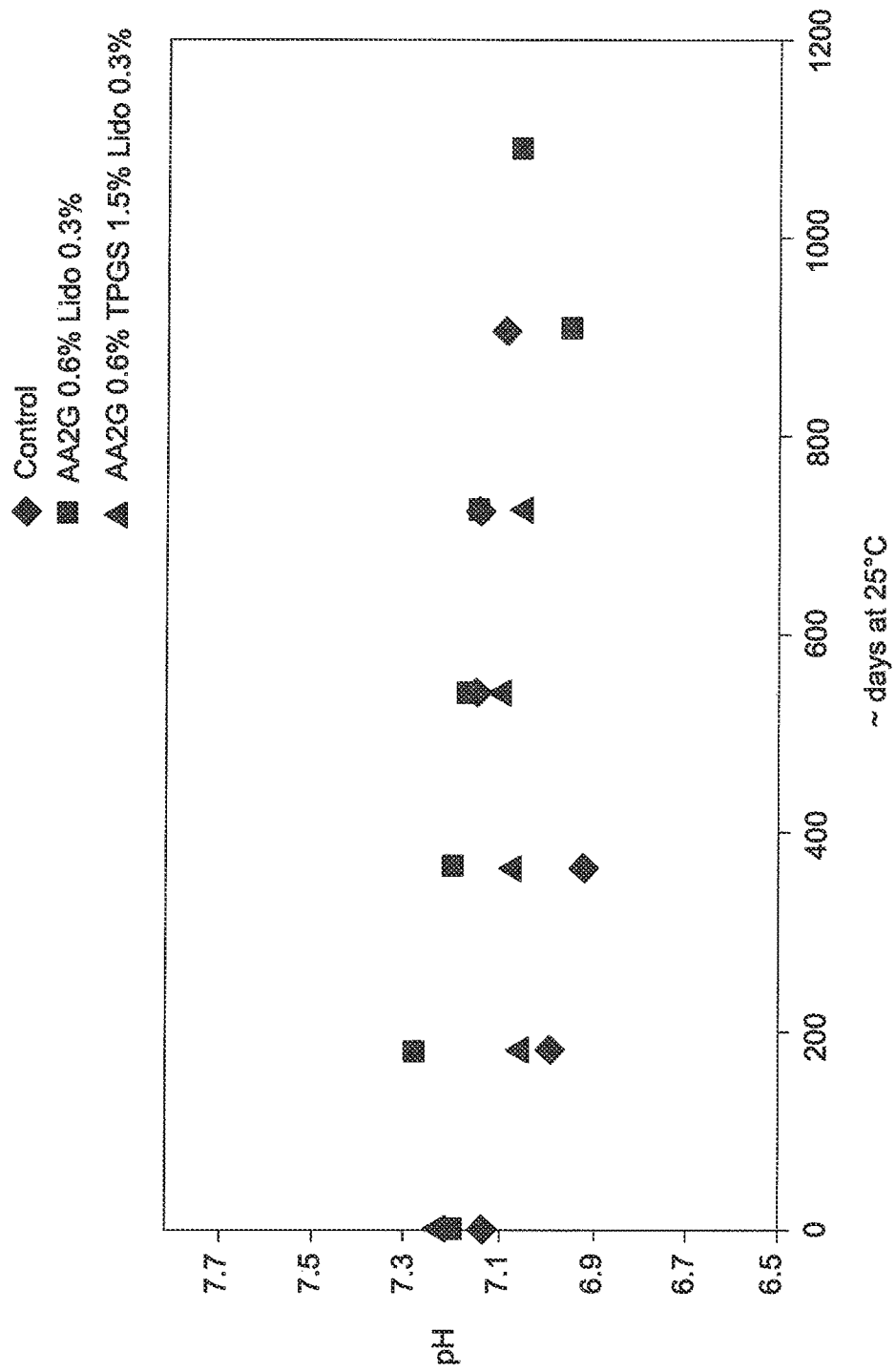
FIG. 4 is a graph showing the pH over time (3 yr equivalent at 25° C.) in compositions: control, AA2G™ plus lidocaine, and AA2G™ plus lidocaine and TPGS.
Figure 5:
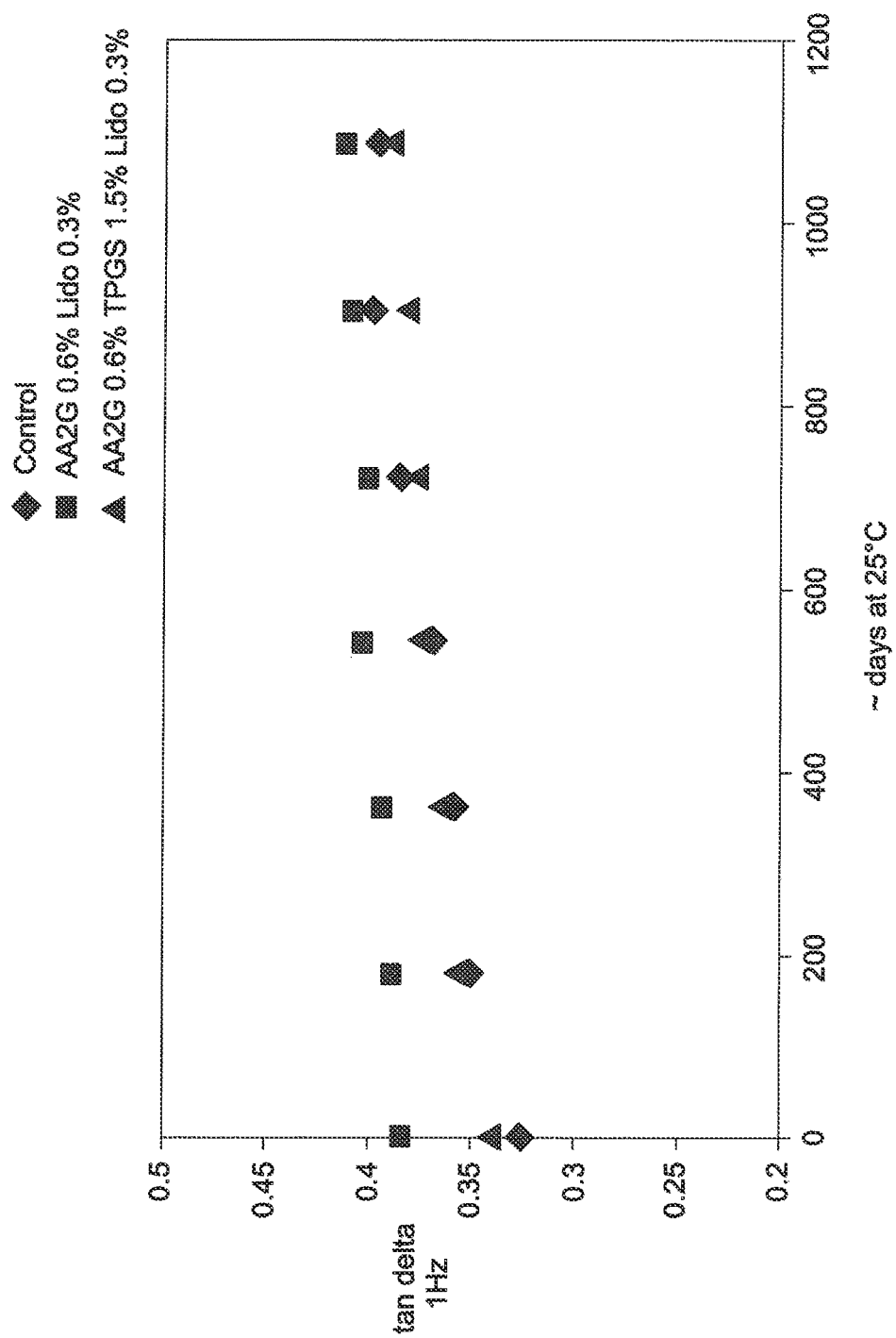
FIG. 5 is a graph of tan delta 1 Hz over time (3 yr equivalent at 25° C.) in compositions: control, AA2G™ plus lidocaine, and AA2G™ plus lidocaine and TPGS.
Figure 6:
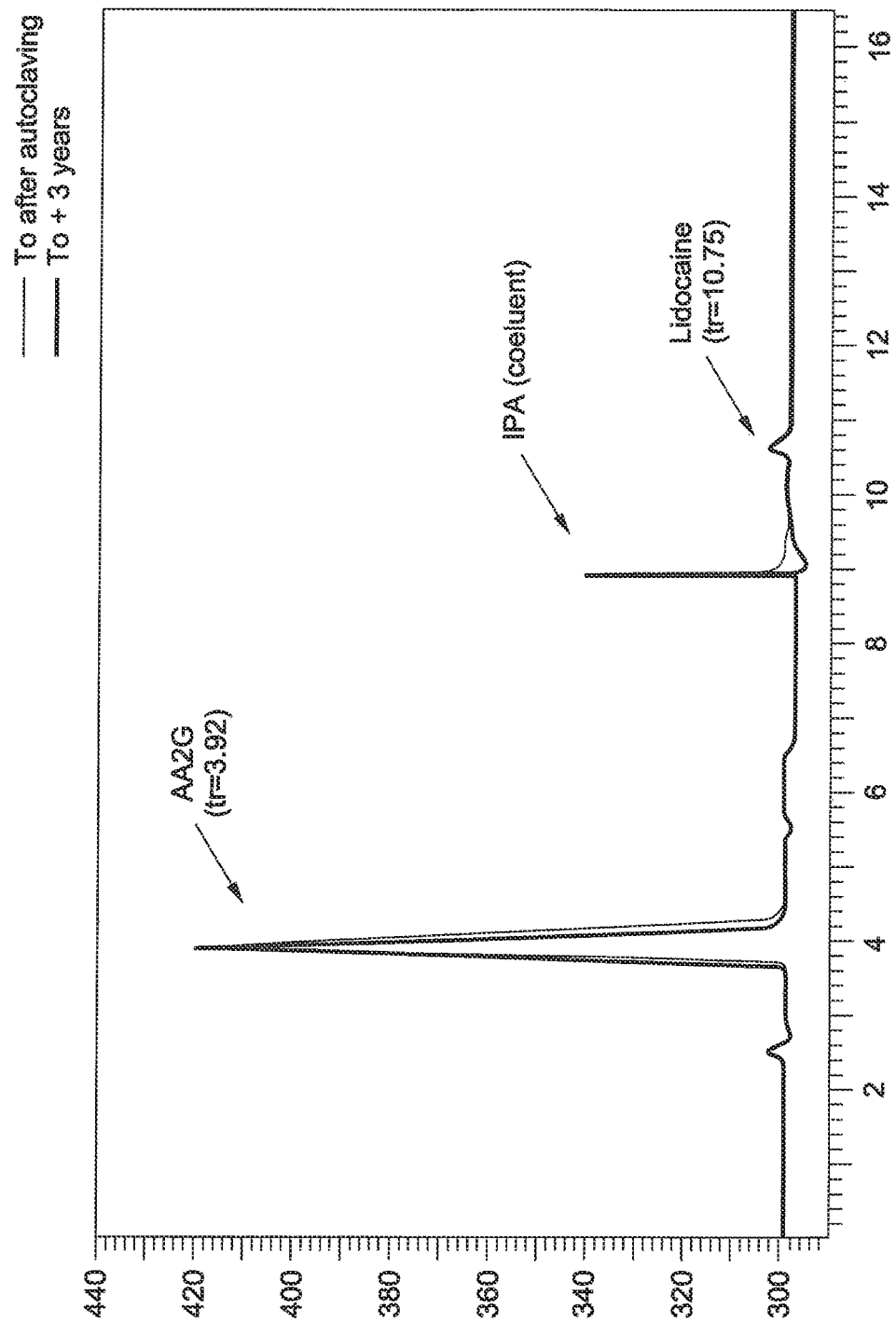
FIG. 6 is an HPLC analysis (C18 column, eluent: sodium phosphate buffer (pH=2.2)/2-propanol 10%, 0.7 ml/min; detection at 260 nm) of AA2G™, lidocaine, and IPA (coeluent) after autoclaving (3 yr equivalent at 25° C.).

The stability of various formulations was tested. The ingredients shown in Table 11 were incorporated into a NaHA matrix, and autoclaved. The degradation of the formulations after autoclaving is shows in Table 11 and after 48 days at 45° C. in Table 12. The stability of extrusion force, pH, and degradation are shown over time in FIGS. 3, 4, and 5, respectively. HPLC analysis (C18 column; eluent: sodium phosphate buffer (pH 2.2), 2-propanol 10%, 0.7 ml/min; detection at 260 nm) confirmed the ingredients after autoclaving and 3-year shelf-life are shown in FIG. 6.

TABLE 11

| | Δ Tan δ 1 Hz | |
|---|---|---|
| | After autoclaving | 45° C., 48 days |
| JUVEDERM ® Ultra Plus + AA2G ™ 0.6% + Lidocaine 0.3% | 0.059 | 0.020 |
| JUVEDERM ® Ultra Plus + AA2G ™ 0.6% + TPGS 1.5% + lidocaine 0.3% | 0.016 | 0.007 |

Example 12

AA2G™ Promotes Collagen Synthesis

Figure 2:
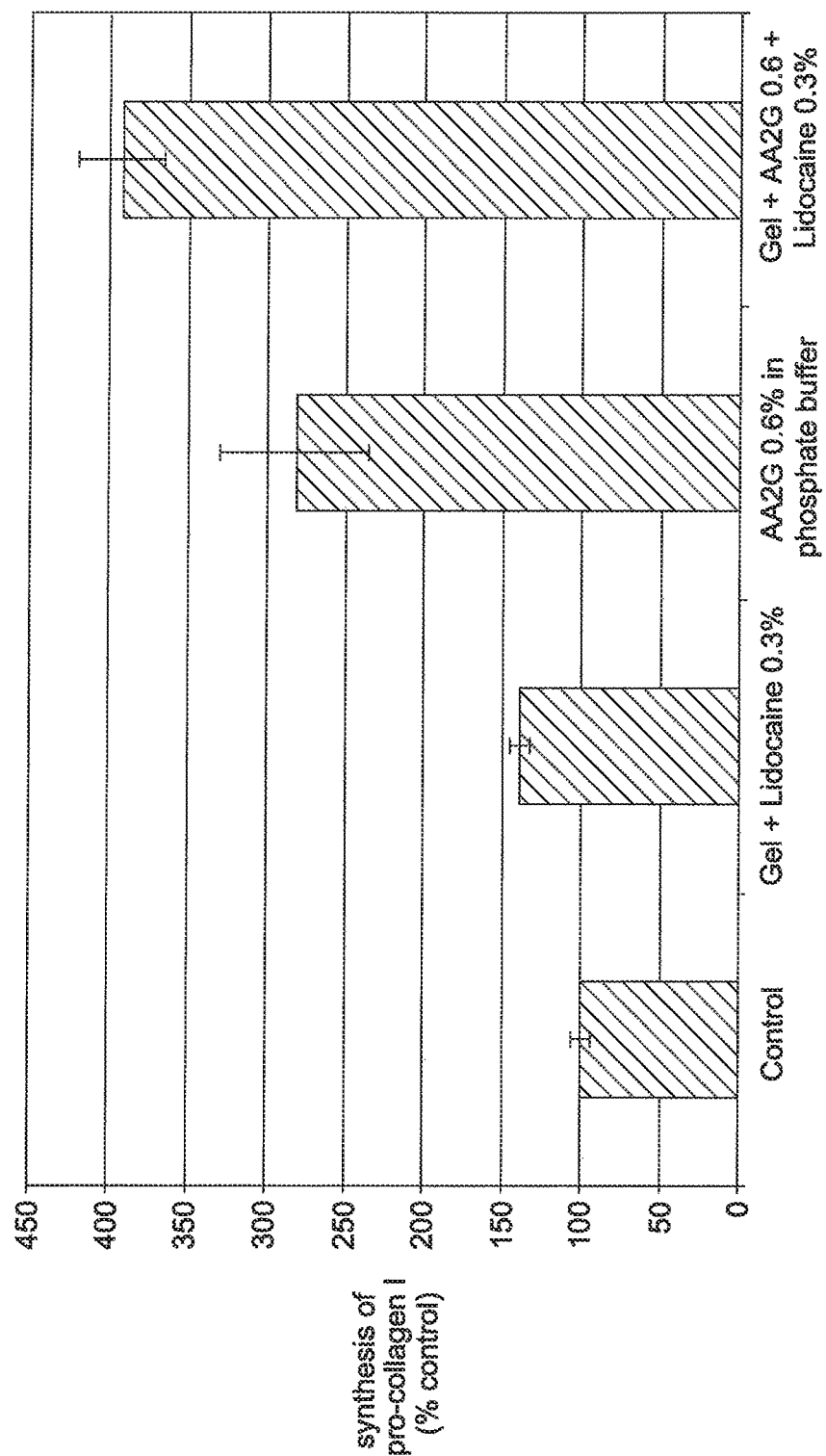
FIG. 2 is a graph showing the synthesis of pro-collagen (% control) for control, gel+lidocaine 0.3%, AA2G™ 0.6% in phosphate buffer, and gel+AA2G™ 0.6%+lidocaine 0.3%.

Human skin fibroblasts were cultured in a 12 wells plate. At confluence, 100 μL of each compound (Juvederm® FORMA with 0.3% lidocaine, Juvederm® FORMA+ AA2G™ 0.6%+Lidocaine 0.3% and Phosphate Buffer with 0.6% AA2G) was deposited in a culture insert (porosity of 0.4 μm), which was itself laid on the fibroblast monolayers. In parallel, a control without treatment was performed. Cultures were incubated for 72 hours and each experimental condition was conducted done in triplicate. At the end of incubation, cell viability was verified by microscopic observation and MTT reduction assay. Pro-collagen I secretion was measured using ELISA kit. The presence of 0.6% AA2G™ in a hyaluronic acid gel containing 0.3% lidocaine increased pro-collagen synthesis by a factor 3 (+292%), whereas JUVEDERM® gel with 0.3% lidocaïne showed an increase of 40% of the pro-collagen secretion (see FIG. 2).

Example 13

AA2G™ Protects NaHA from Oxidative Degradation

The effect of AA2G™ on NaHA oxidative degradation was studied. Oxidation testing was used as it allows testing of the resistance of a NaHA matrix to free radicals. Degradation by free radicals was simulated on a rheometer (Haake Rheostress 600) by addition of 1/7 ratio of $H_2O_2$ 30% on the surface of a spread gel measured with a controlled stress rheometer according to the following method: frequency of 1 Hz with 0.8% controlled strain, during 3600 s at 35° C. The time value is taken at 5 Pa/s.

Figure 7:
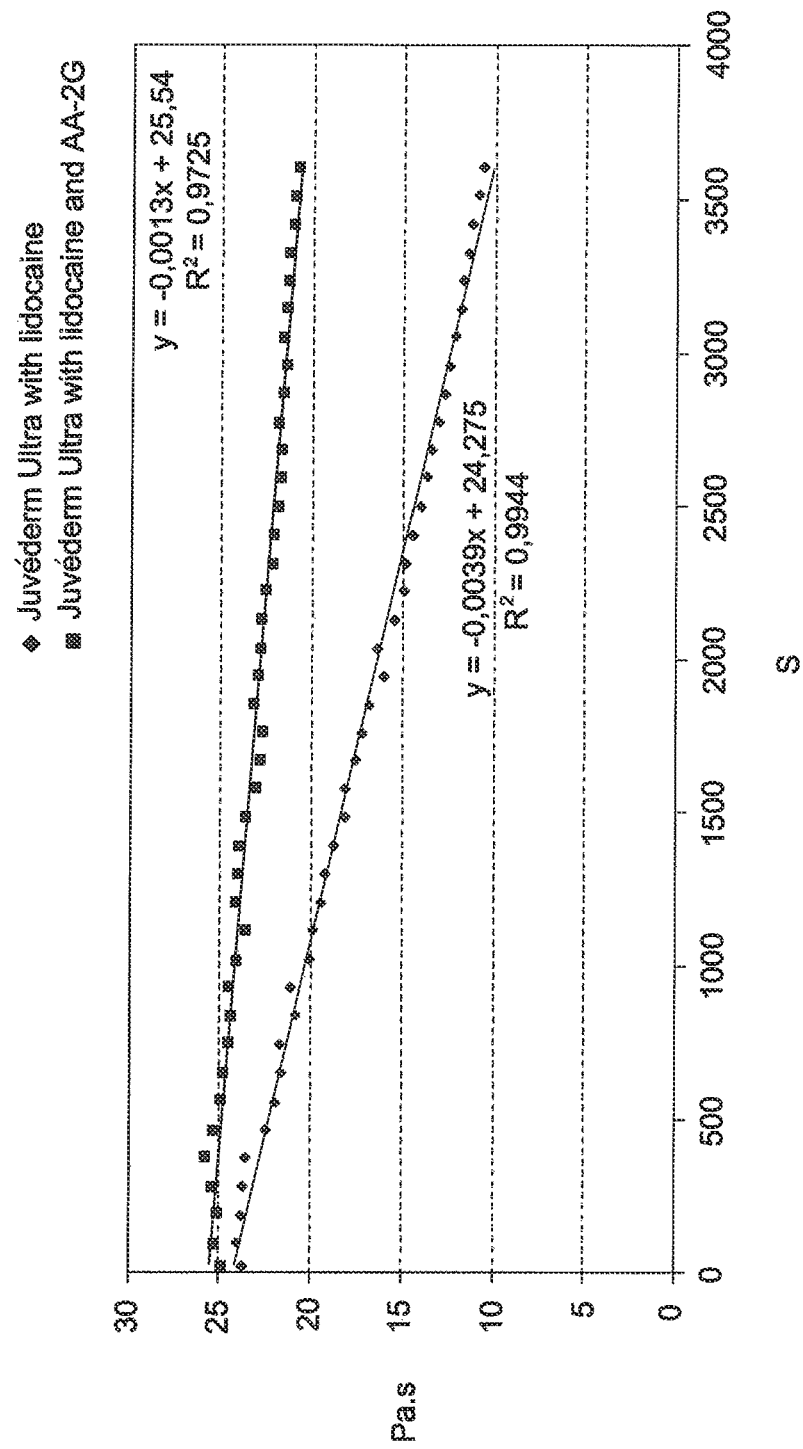
FIG. 7 is a graph comparing antioxidant properties in compositions: control versus JUVEDERM® Ultra with lidocaine AA2G™, and JUVEDERM® Ultra with lidocaine.

Further, a comparison of antioxidant properties for JUVEDERM® Ultra with AA2G™ 0.6%/Lidocaine 0.3% formulation (15 800 s) versus NaHA matrix JUVEDERM® Ultra with Lidocaine (4 942 s) showed that the gel containing AA2G™ and lidocaine is more stable with respect to free radical activity (see FIG. 7). AA2G™ protected against oxidative degradation by a factor of 3.

Example 14

Implantation Study

A gel containing AA2G™ at 0.6% (=6 mg/g=$2.10^{-2}$ mM) was implanted in the deep dermis and subcutaneous tissues in rats. Histological evaluation at 1 week showed some mononuclear cells (lymphocytes and plasmocytes) around the implants in all implantation sites (test and control). They were also associated with macrophages. The gel containing AA2G™ appeared to be less inflammatory. The irritation index in test samples (AA2G™+NaHA) was 9.9 compared to 12.3 in controls (NaHA only). Table 12 shows the histological results at 1 week, 1 month, and 3 months. The irritation score of AA2G™ gel are (for each implantation time) lower than control (gel without AA2G™)

TABLE 12

| | NAHA + AA2G + Lido |
|---|---|
| Biocompatibility ISO 10993 | |
| Cytotoxicity | ✓ (non cytotoxic) |
| Irritation | ✓ (non irritant) |
| Sensitization | ✓ (non sensitizing) |

TABLE 12-continued

| | NAHA + AA2G + Lido |
|---|---|
| Implantation Test | |
| 1 week | ✓ (no skin reaction) |
| 3 weeks | ✓ (no skin reaction) |
| 3 months | ✓ (no skin reaction) |

Example 15

Incorporation of Dexpanthenol in NaHA Gel Formulations

Dexpanthenol was incorporated into a NaHA matrix JUVEDERM® Ultra Plus with Lidocaine (with 0.3% w/w lidocaine) with a content of 1 w/w. The gel was autoclaved. The gel obtained was clear and uncolored before and after autoclaving. The gel properties after autoclaving are shown in Table 13.

TABLE 13

| | After autoclaving | |
|---|---|---|
| Formulation | Extrusion force (N) | Δ Tan δ 1 Hz |
| JUVEDERM ®Ultra Plus with Lidocaine (0.3%) + Dexpanthenol 1% | PASSED | 0.026 |

Example 16

Effect of the Incorporation of Dexpanthenol in NAHA Gel Formulations

The shelf-life at 45° C. during 30 days was tested of the formulations prepared in example 15 and the NaHA matrix JUVEDERM® Ultra Plus XC. The gel was clear, uncolored. Rheology data of the gels containing dexpanthenol 1% w/w and lidocaine 0.3% w/w are shown in Table 14.

TABLE 14

| Formulation | After 30 days at 45° C. Δ Tan δ 1 Hz |
|---|---|
| JUVEDERM ®Ultra Plus with Lidocaine (0.3%) + Dexpanthenol 1% | −0.071 |

Rheological studies showed an increase of the stability of the gel in the presence of the additive.

Example 17

Incorporation of Epinephrine in NaHA Gel Formulations

Epinephrine was incorporated into a NaHA matrix (JUVEDERM® Ultra Plus) with a 10 ppm epinephrine bitartrate. The gel was autoclaved. The gel obtained was clear and uncolored before and after autoclaving. The gel (dermal filler formulation) properties after autoclaving are shown in Table 15.

TABLE 15

| Formulation | After autoclaving | |
| --- | --- | --- |
| | Extrusion force (N) | Δ Tan δ 1 Hz |
| JUVEDERM ® Ultra Plus + epinephrine bitartrate 10 ppm | PASSED | 0.165 |

Degradation of the gel was observed by rheological analysis.

Example 18

Incorporation of Epinephrine in NaHA Gel Formulations

Epinephrine was incorporated into a NaHA matrix (JUVEDERM® Ultra Plus) with 0.3% lidocaine and 10 ppm epinephrine bitartrate. The gel was autoclaved. The gel obtained was clear and colored after autoclaving. The gel properties after autoclaving are shown in Table 16.

TABLE 16

| Formulation | After autoclaving | |
| --- | --- | --- |
| | Extrusion force (N) | Δ Tan δ 1 Hz |
| JUVEDERM ®Ultra Plus + Lidocaine 0.3% + epinephrine bitartrate 10 ppm | PASSED | 0.092 |

A slight degradation of the gel was observed by rheological analysis.

Example 19

Effect of Additional Ingredient on the Stability of Gel Containing Epinephrine and Lidocaine The shelf-life at 45° C. during 60 days was tested of the formulations prepared in Example 18 and the NaHA matrix JUVEDERM® Ultra Plus. The gel was clear, slightly colored. Rheology data of the gels containing epinephrine bitartrate (10 ppm), lidocaine (0.3% w/w) is shown in Table 17.

TABLE 17

| Formulation | After 60 days at 45° C. Δ Tan δ 1 Hz |
| --- | --- |
| JUVEDERM ®Ultra Plus + Lidocaine 0.3% + epinephrine bitartrate 10 ppm | 0.185 |

After a stability of 60 days at 45° C., the gel containing epinephrine and lidocaine was unstable.

Example 20

Incorporation of Epinephrine in NaHA Gel Formulations Containing an Antioxidant Epinephrine was incorporated into a NaHA matrix (JUVEDERM® Ultra Plus) with epinephrine bitartrate (10 ppm) and mannitol (0.9 or 4.5% w/w). The gels were autoclaved. The gel with 4.5% mannitol was clear and uncolored before and after autoclaving whereas with 0.9% mannitol was slightly colored. The gel properties after autoclaving is shown in Table 18.

TABLE 18

| Formulation | After autoclaving | |
| --- | --- | --- |
| | Extrusion force (N) | Δ Tan δ 1 Hz |
| JUVEDERM ® Ultra Plus + epinephrine bitartrate 10 ppm + mannitol 0.9% | PASSED | 0.047 |
| JUVEDERM ® Ultra Plus + epinephrine bitartrate 10 ppm + mannitol 4.5% | PASSED | 0.015 |

No degradation was observed for either of the dermal filler formulations tested.

Example 21

Effect of Additional Ingredient on the Stability of Gel Containing Epinephrine and an Antioxidant The shelf-life at 45° C. during 60 days was tested of the formulations prepared in example 20 and the NaHA matrix JUVEDERM® Ultra Plus. The gels were clear, slightly colored. Rheology data of the gels containing epinephrine bitartrate (10 ppm) and mannitol (0.9 or 4.5% w/w) is shown in Table 19.

TABLE 19

| Formulation | After 60 days at 45° C. Δ Tan δ 1 Hz |
| --- | --- |
| JUVEDERM ® Ultra Plus + epinephrine bitartrate 10 ppm + mannitol 0.9% | 0.061 |
| JUVEDERM ® Ultra Plus + epinephrine bitartrate 10 ppm + mannitol 4.5% | 0.006 |

After a stability of days at 45° C., both gels containing epinephrine, lidocaine and mannitol were stable. The composition containing 4.5% mannitol was more stable.

Example 22

Incorporation of Epinephrine in NaHA Gel Formulations Containing Lidocaine and Antioxidant Epinephrine was incorporated into a NaHA matrix (JUVEDERM® Forma) with epinephrine bitartrate (20 ppm), lidocaine (0.3% w/w) and mannitol (4.5% w/w). The gel was autoclaved. The gel obtained was clear slightly colored after autoclaving. The gel properties after autoclaving are shown in Table 20.

TABLE 20

| Formulation | After autoclaving | |
| --- | --- | --- |
| | Extrusion force (N) | Δ Tan δ 1 Hz |
| JUVEDERM ® Forma + Lidocaine 0.3% + epinephrine bitartrate 20 ppm + mannitol 4.5% | PASSED | 0.026 |

No degradation was observed.

Example 23

Effect of Additional Ingredient on the Stability of Gel Containing Epinephrine, Lidocaine and an Antioxidant The shelf-life at 45° C. during 60 days was tested of the formulations prepared in example 22 and the NaHA matrix JUVEDERM® Forma. The gel was clear, slightly colored. Rheology data of the gel containing epinephrine bitartrate (20 ppm), lidocaine (0.3% w/w) and mannitol (4.5% w/w) is shown in Table 21.

TABLE 21

| Formulation | After 60 days at 45° C. Δ Tan δ 1 Hz |
|---|---|
| JUVEDERM ® Forma + epinephrine bitartrate 20 ppm + mannitol 4.5% | −0.030 |

The gel (dermal filler formulation) was stable after 60 days at 45° C.

Example 24

Incorporation of Synephrine in NaHA Gel Formulations Containing Lidocaine and Antioxidant Synephrine was incorporated into a NaHA matrix Juvederm Ultra Plus with Lidocaine (with 0.3% w/w lidocaine) with a content of 100 ppm of synephrine. The gel was autoclaved. The gel obtained was clear and uncolored before and after autoclaving. The gel properties after autoclaving is shown in Table 22.

TABLE 22

| | After autoclaving | |
|---|---|---|
| Formulation | Extrusion force (N) | Δ Tan δ 1 Hz |
| JUVEDERM ®with lidocaine (0.3%) + synephrine 100 ppm | PASSED | −0.006 |

Example 25

Effect of Additional Ingredient on the Stability of Gel Containing Synephrine and Lidocaine The shelf-life at 45° C. during 60 days was tested of the formulations prepared in example 24 and the NaHA matrix JUVEDERM® Ultra Plus with Lidocaine. The gels was clear, uncolored. Rheology data of the gel containing synephrine 100 ppm and lidocaine 0.3% w/w is shown in Table 23.

TABLE 23

| Formulation | After 60 days at 45° C. Δ Tan δ 1 Hz |
|---|---|
| JUVEDERM ®Ultra Plus with lidocaine (0.3%) + synephrine 100 ppm | −0.028 |

This rheological study showed maintenance of the stability of the gel (dermal filler formulation) in the presence of the particular additional ingredient (additive) shown.

Example 26

Incorporation of Phenylephrine in NaHA Gel Formulations Containing Lidocaine

Phenylephrine was incorporated into a matrix JUVEDERM® Ultra Plus with Lidocaine (with 0.3% w/w lidocaine) with a content of 100 ppm phenylephrine. The gel was autoclaved. The gel obtained was clear and uncolored before and after autoclaving. The gel properties after autoclaving are shown in Table 24.

TABLE 24

| | After autoclaving | |
|---|---|---|
| Formulation | Extrusion force (N) | Δ Tan δ 1 Hz |
| JUVEDERM ® Ultra Plus with Lidocaine 0.3% + Phenylephrine 100 ppm | PASSED | −0.002 |

Example 27

Effect of Additional Ingredient on the Stability of Gel Containing Phenylephrine and Lidocaine The shelf-life at 45° C. during 60 days was tested of the formulations prepared in example 26 and the NaHA matrix JUVEDERM® Ultra Plus with Lidocaine. The gel was clear, uncolored. Rheology data of the gel containing phenylephrine 100 ppm and lidocaine 0.3% w/w are shown in Table 25.

TABLE 25

| Formulation | After 60 days at 45° C. Δ Tan δ 1 Hz |
|---|---|
| JUVEDERM ® Ultra Plus with Lidocaine (0.3%) + Phenylephrine 100 ppm | −0.017 |

This rheological study showed maintenance of the stability of the gel (dermal filler formulation) in the presence of the particular additional ingredient (additive) shown.

Example 28

Incorporation of Naphazoline in NaHA Gel Formulations Containing Lidocaine and Antioxidant Naphazoline was incorporated into a matrix Juvederm Ultra Plus with Lidocaine (with 0.3% w/w lidocaine) with a content of 100 ppm. The gel was autoclaved. The gel obtained was clear and uncolored before and after autoclaving. The gel properties after autoclaving are shown in Table 26.

TABLE 26

| | After autoclaving | |
|---|---|---|
| Formulation | Extrusion force (N) | Δ Tan δ 1 Hz |
| JUVEDERM ® Ultra Plus with Lidocaine (0.3%) + Naphazoline 100 ppm | PASSED | −0.003 |

Example 29

Effect of Additional Ingredient on the Stability of Gel Containing Naphazoline and Lidocaine The shelf-life at 45° C. over 60 days was tested of the formulations prepared in example 28 and the NaHA matrix JUVEDERM® Ultra Plus with Lidocaine. The gel was clear, uncolored. Rheology data of the gel containing naphazoline 100 ppm and lidocaine 0.3% w/w is shown in Table 27.

TABLE 27

| Formulation | After 60 days at 45° C. Δ Tan δ 1 Hz |
|---|---|
| JUVEDERM ® Ultra Plus with Lidocaine 0.3% + Naphazoline 100 ppm | −0.008 |

Example 30

Treatment Example

A woman, age 37, presents with fine lines around her eyes and deeper wrinkles on the sides of her mouth. She receives injections of a formulation of Example 10. She receives the injections in the fine lines and in the wrinkles once a week for 3 weeks and notices a visible improvement in the appearance of her skin.

Example 31

Alternate Treatment Example

A 59 year old man presents with wrinkles between his eyebrows and in the nasolabial folds. He receives injections of the dermal filler formulation of Example 11, every 3 months. A visible improvement in the wrinkles is seen.

Example 32

Alternate Treatment Example

A 35 year old woman presents with fine lines across her forehead. She receives injections of the dermal filler formulation of Example 15, once a week for two weeks, and notices an improvement in the appearance of the skin on her forehead.

Example 33

Alternate Treatment Example

A woman, age 44, presents with uneven texture on her right cheek resulting from a loss of collagen due to aging. She receives injections of the dermal formulation of Example 20 (using the 4.5% mannitol dermal filler formulation), in her cheek to build up the areas where the collagen has been lost. A visible improvement is seen in the texture of the skin on her cheek after 3 series of injections over a 2 week period of time.

Example 34

Alternate Treatment Example

A 35 year old man presents with a deep wrinkle across his chin and fine lines on the sides of his eyes. He receives the dermal filler formulation of Example 26 along the sides of his eyes. He receives 2 series of injections in his chin, spaced 1 week apart. The fine lines and wrinkle are visibly diminished after treatment.

Example 35

Alternate Treatment Example

A woman, age 62, presents with wrinkles across her forehead, on the sides of her eyes, in the nasolabial folds, and a scar on her chin. She receives injections of the dermal filler formulation of Example 29 each week for one month. After the injections, the appearance of the wrinkles and the scar is visibly diminished.

Our results above show that at least each of the two additional ingredients AA2G and dexpanthenol significantly increased the stability of the dermal filler formulation (HA gel), as shown by the dermal filler formulation having a Δ Tan δ 1 Hz<−0.05.

With regard to dexpanthenol: panthenol is the alcohol analog of pantothenic acid (vitamin B5), and is thus the provitamin of B5 which in vivo is oxidized to pantothenate. Panthenol is a highly viscous transparent liquid at room temperature, but salts of pantothenic acid (for example sodium pantothenate) are powders (typically white). Panthenol is soluble in water, alcohol and propylene glycol, soluble in ether and chloroform, and slightly soluble in glycerin. Panthenol has two D and L enantiomers with only the D enantiomer (D-panthenol, also called dexpanthenol) being biologically active, however both the D and L forms have moisturizing properties. For topical cosmetic use panthenol has been used in the D form and as a racemic mixture of D and L (DL-panthenol). Thus topical dexpanthenol cream (sold under the generic name "panthoderm") is made by mixing with an emollient and has been used for relieving dry skin, preventing and treating sore nipples during breast-feeding, and promoting healing of burns and poorly-healing wounds.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein. Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described. Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

We claim:

1. A steam sterilization-stable dermal filler formulation comprising a crosslinked hyaluronic acid (HA), ascorbyl-2-glucoside and an anesthetic agent, wherein the hyaluronic acid is crosslinked with 1,4-butanediol diglycidyl ether, 1,4-bis(2,3-epoxypropoxy)butane, 1,4-bisglycidyloxybutane, 1,2-bis(2,3-epoxypropoxy)ethylene, or 1-(2,3-epoxypropyl)-2,3-epoxycyclohexane.

2. The dermal filler formulation of claim 1, wherein the anesthetic agent is lidocaine.

3. The dermal filler formulation of claim 2, wherein the lidocaine is present in an amount of about 0.001% to about 10% w/w.

4. The dermal filler formulation of claim 2, wherein the lidocaine is present in an amount of about 0.001% to about 5% w/w.

5. The dermal filler formulation of claim 2, wherein the lidocaine is present in an amount of about 0.3% to about 3% w/w.

6. The dermal filler formulation of claim 2, wherein the lidocaine is present in an amount of 0.3% w/w.

7. The dermal filler formulation of claim 1, wherein the crosslinked HA is present in an amount of about 1 mg/mL to about 40 mg/mL.

8. The dermal filler formulation of claim 7, wherein the crosslinked HA is present in an amount of about 10 mg/mL to about 40 mg/mL.

9. The dermal filler formulation of claim 7, wherein the crosslinked HA is present in an amount of about 20 mg/mL to about 30 mg/mL.

10. The dermal filler formulation of claim 7, wherein the crosslinked HA is present in an amount of about 20 mg/mL to about 25 mg/mL.

11. The dermal filler formulation of claim 1, wherein the ascorbyl-2-glucoside is present in an amount of about 0.001% w/w to about 10% w/w.

12. The dermal filler formulation of claim 11, wherein the ascorbyl-2-glucoside is present in an amount of about 0.1% w/w to about 3.0% w/w.

13. The dermal filler formulation of claim 11, wherein the ascorbyl-2-glucoside is present in an amount of 1% w/w.

14. The dermal filler formulation of claim 11, wherein the ascorbyl-2-glucoside is present in an amount of 2% w/w.

15. The dermal filler formulation of claim 11, wherein the ascorbyl-2-glucoside is present in an amount of 0.6% w/w.

16. The dermal filler formulation of claim 1, wherein the steam-sterilization stability of the dermal filler formulation is determined by subjecting the dermal filler formulation to a steam sterilization treatment at between about 120° C. and about 135° C. for between about 1 minute and about 5 minutes, with substantial retention after the treatment of one or more of the dermal filler characteristics of being clear, homogenous and cohesive.

17. The dermal filler formulation of claim 16, wherein the HA is crosslinked with 1,4-butanediol diglycidyl ether, and the anesthetic agent is lidocaine.

18. The dermal filler formulation of claim 17, wherein the crosslinked HA is present in an amount of about 10 mg/mL to about 40 mg/mL.

19. The dermal filler formulation of claim 18, wherein the ascorbyl-2-glucoside is present in an amount of about 0.1% w/w to about 3.0% w/w, and the lidocaine is present in an amount of about 0.3% to about 3% w/w.

\* \* \* \* \*